United States Patent [19]

Dinsmore et al.

[11] Patent Number: 5,710,171
[45] Date of Patent: Jan. 20, 1998

[54] BISPHENYL INHIBITORS OF FARNESYL-PROTEIN TRANSFERASE

[75] Inventors: Christopher J. Dinsmore, North Wales; Suzanne C. MacTough, Chalfont; Gerald E. Stokker, Gwynedd Valley; Theresa M. Williams, Harleysville, all of Pa.

[73] Assignee: Merck & Co., Inc., Rahway, N.J.

[21] Appl. No.: 648,330

[22] Filed: May 15, 1996

Related U.S. Application Data

[63] Continuation-in-part of Ser. No. 449,038, May 24, 1995, abandoned.

[51] Int. Cl.$^6$ ............... A61K 31/415; C07D 403/02; C07D 233/56; C07D 233/61; C07D 233/60; C07D 233/54
[52] U.S. Cl. ............... 514/396; 514/397; 514/399; 514/400; 548/312.7; 548/335.1; 548/335.5; 548/338.1; 548/341.1
[58] Field of Search ................... 514/396, 397, 514/400, 399; 548/312.7, 338.1, 335.1, 335.5, 341.1

[56] References Cited

U.S. PATENT DOCUMENTS

| | | | |
|---|---|---|---|
| 5,043,268 | 8/1991 | Stock | 514/397 X |
| 5,141,851 | 8/1992 | Brown et al. | 514/397 X |
| 5,238,922 | 8/1993 | Graham et al. | 514/397 X |
| 5,326,773 | 7/1994 | De Solms et al. | 514/397 X |
| 5,326,776 | 7/1994 | Winn et al. | 514/382 |
| 5,340,828 | 8/1994 | Graham et al. | 514/397 X |
| 5,352,705 | 10/1994 | Deana et al. | 514/397 X |
| 5,504,212 | 4/1996 | De Solms et al. | 514/397 X |
| 5,534,537 | 7/1996 | Ciccarone et al. | 514/397 |

FOREIGN PATENT DOCUMENTS

| | | | |
|---|---|---|---|
| 0 456 180 A1 | 11/1991 | European Pat. Off. | 514/397 |
| WO 91/16340 | 10/1991 | WIPO | 514/397 |
| WO 93/13075 | 12/1991 | WIPO . | |
| WO 95/00493 | 6/1993 | WIPO . | |
| WO 93/13075 | 7/1993 | WIPO | 514/397 |
| WO 95/00493 | 1/1995 | WIPO | 514/397 |
| WO 95/11917 | 5/1995 | WIPO | 514/397 |
| WO 95/25086 | 9/1995 | WIPO | 514/397 |
| WO 96/34851 A | 11/1996 | WIPO . | |

OTHER PUBLICATIONS

Gibbs, J.B. et al., "Selective Inhibition of Farnesyl-Protein Transferase Blocks Ras Processing in Vivo," The Journal of Biological Chemistry, vol. 268, No. 11, pp. 7617-7620 (1993).

Goldstein, J.L. et al., "Nonfarnesylated Tetrapeptide Inhibitors of Protein Farnesyltransferase," The Journal of Biological Chemistry, vol. 266, No. 24, pp. 15575-15578 (1991).

James, G.L. et al., "Benzodiazepine Peptidomimetic BZ-5B Interrupts the MAP Kinase Activation Pathway in H-Ras-transformed Rat-1 Cells, but Not in Untransformed Cells," The Journal of Biological Chemistry, vol. 369, No. 44, pp. 27705-27714 (1994)

James, G.L. et al., "Benzodiazepine Peptidomimetics: Potent Inhibitors of Ras Farnesylation in Animal Cells", Science, vol. 260, pp. 1937-1942 (1993).

James, G., et al., "Polylysine and CVIM Sequences of K-RasB Dictate Specificity of Prenylation and Confer Resistance to Benzodiazepine Peptidomimetic in Vitro", The Journal of Biological Chemistry, vol. 270, No. 11, pp. 6221-6226 (1995).

Kohl, N.E., et al., "Inhibition of farnesyltransferase induces regression of mammary and salivary carcinomas in ras transgenic mice," Nature Medicine, vol. 1, No. 8, pp. 792-797 (1995).

Kohl, N.E. et al., "Selective Inhibition of ras-Dependent Transformation by a Farnesyltransferase Inhibitor", Science, vol. 260, pp. 1934-1937 (1993).

Kohl, N.E. et al., "Protein farnesyltransferase inhibitors block the growth of ras-dependent tumors in nude mice", Proc. Natl. Acad. Sci. USA, Med. Sciences, vol. 91, pp. 9141-9145 (1994).

Nigam, M., et al., "Potent Inhibition of Human Tumor p21 ras Farnesyltransferase by A1A2-lacking p21 ras CA1A2X Peptidomimetics", The Journal of Biol. Chem., vol. 268, Issue of Oct. 5, pp. 20695-20698 (1993).

Pompliano, D.L., "Steady-State Kinetic Mechanism of Ras Farnesyl:Protein Transferase", Biochemistry, vol. 31, pp. 3800-3807 (1992).

Qian, T., et al., "Design and Structural Requirements of Potent Peptidomimetic Inhibitors of p21 ras Farnesyltransferase", The Journal of Biol. Chem., vol. 269, No. 17, Issue of Apr. 29, pp. 12410-12413 (1994).

Vogt, A., et al. "A Non-peptide Mimetic of Ras-CAAX: Selective Inhibition of Farnesyltransferase and Ras Processing", The Journal of Biol. Chem., vol. 270, No. 2, Issue of Jan. 13, pp. 660-664 (1995).

(List continued on next page.)

Primary Examiner—Floyd D. Higel
Attorney, Agent, or Firm—David A. Muthard; Mark R. Daniel

[57] ABSTRACT

The present invention comprises peptidomimetic compounds which comprise a suitably substituted aminoalkylbenzene and analine analogs, further substituted with a second phenyl ring attached via a bond, a heteroatom linker or an aliphatic linker. The instant compounds inhibit the farnesyl-protein transferase enzyme and the farnesylation of certain proteins. Furthermore, the instant farnesyl protein transferase inhibitors differ from those previously described as inhibitors of farnesyl-protein transferase in that they do not have a thiol moiety. The lack of the thiol offers unique advantages in terms of improved pharmacokinetic behavior in animals, prevention of thiol-dependent chemical reactions, such as rapid autoxidation and disulfide formation with endogenous thiols, and reduced systemic toxicity. Further contained in this invention are chemotherapeutic compositions containing these farnesyl transferase inhibitors and methods for their production.

26 Claims, No Drawings

OTHER PUBLICATIONS

Bernhard, E.J., et al., "The Farnesyltransferase Inhibitor FTI–277 Radiosensitizes H–ras–transformed Rat Embryo Fibroblasts," Cancer Research, vol. 56, pp. 1727–1730 (1996).

Lerner, E.C., et al., "Disruption of Oncogenic K–Ras4B Processing and Signaling by a Potent Geranylgeranyltransferase I Inhibitor," Jour. Biol. Chem., vol. 270, No. 45, pp. 26770–26773 (1995).

Lerner, E.C., et al., "Ras CAAX Peptidomimetic FTI–277 Selectively Blocks Oncogenic Ras Signaling by Inducing Cytoplasmic Accumulation of Inactive Ras–Raf Complexes," Jour. of Biol. Chem., vol. 270, No. 45, pp. 26802–26806 (1995).

Sepp–Lorenzino, L., et al., "A Peptidomimetic Inhibitor of Farnesyl:Protein Transferase Blocks the Anchorage–dependent and –independent Growth of Human Tumor Cell Lines," Cancer Research, vol. 55, pp. 5302–5309 (1995).

Sun, J., et al., "Ras CAAX Peptidomimetic FTI276 Selectively Blocks Tumor Growth in Nude Mice of a Human Lung Carcinoma with K–Ras Mutation and p53 Deletion," Cancer Research, vol. 55, pp. 4243–4247 (1995).

BISPHENYL INHIBITORS OF FARNESYL-PROTEIN TRANSFERASE

RELATED APPLICATION

The present patent application is a continuation-in-part application of application Ser. No. 08/449,038, filed May 24, 1995, now abandoned.

BACKGROUND OF THE INVENTION

The Ras protein is part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science,* 260:1934–1937 (1993) and G. L. James et al., *Science,* 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.,* 91:9141–9145 (1994).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell,* 62:81–88 (1990); Schaber et al., *J. Biol. Chem.,* 265:14701–14704 (1990); Schafer et al., *Science,* 249:1133–1139 (1990); Manne et al., *Proc. Natl. Acad. Sci USA,* 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. In the peptide derived class of inhibitors, a subclass of inhibitors has been described which generally comprises cysteine containing molecules that are related to the CAAX motif that is the signal for protein prenylation. (Schaber et al., ibid; Reiss et. al., ibid; Reiss et al., *PNAS,* 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science,* 260:1934–1937 (1993); Graham, et al., *J. Med. Chem.,* 37, 725 (1994)). In general, deletion of the thiol from a peptidyl CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

Another subclass of the peptide derived inhibitors which comprises peptidomimetic compounds wherein the central AA portion of the CAAX motif has been replaced by 3-aminobenzoic acid and 3-aminomethylbenzoic acid spacers has recently been described (M. Nigam et al. *J. Biol. Chem.,* 268:20695–20698 (1993), Y. Qian et al. *J. Biol. Chem.,* 269:12410–124 13 (1994)). FPTase peptidomimetic inhibitors further lacking a C-terminus peptidyl moiety (wherein the X peptide has been replaced by a non-peptide moiety) have also been recently described (A. Vogt et al. *J. Biol. Chem.,* 270:660–664 (1995)). All of the compounds in this second subclass of peptide derived inhibitors retain the thiol moiety.

It is, therefore, an object of this invention to develop non-peptide compounds that do not have a thiol moiety, and that will inhibit farnesyl-protein transferase and thus, the post-translational farnesylation of proteins. It is a further object of this invention to develop chemotherapeutic compositions containing the compounds of this invention and methods for producing the compounds of this invention.

SUMMARY OF THE INVENTION

The present invention includes substituted aminoalkyl-benzene and aniline analogs, further substituted with a second phenyl ting attached via a bond, a heteroatom linker or an aliphatic linker, and related compounds which inhibit the farnesyl-protein transferase. The invention also includes chemotherapeutic compositions containing the compounds of this invention and methods for producing the compounds of this invention. Furthermore these analogs differ from those aminobenzenyl analogs previously described as inhibitors of farnesyl-protein transferase in that they do not have a thiol moiety. The lack of the thiol offers unique advantages in terms of improved pharmacokinetic behavior in animals, prevention of thiol-dependent chemical reactions, such as rapid autoxidation and disulfide formation with endogenous thiols, and reduced systemic toxicity.

The compounds of this invention are illustrated by the formula:

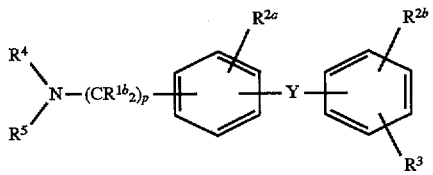

DETAILED DESCRIPTION OF THE INVENTION

The compounds of this invention are useful in the inhibition of farnesyl-protein transferase and the farnesylation of certain proteins. In a first embodiment of this invention, the farnesyl-protein transferase inhibitors are illustrated by the formula I:

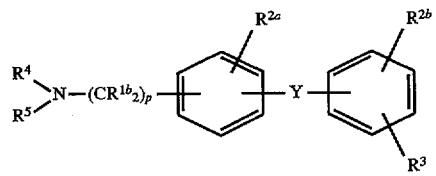

wherein:

$R^{1a}$ and $R^{1b}$ are independently selected from:
a) hydrogen,
b) unsubstituted or substituted aryl, unsubstituted or substituted heterocycle, unsubstituted or substituted $C_3$–$C_6$ cycloalkyl, $C_2$–$C_6$ alkenyl, $C_2$–$C_6$ alkynyl, $R^8O$—, $R^9S(O)_m$—, $R^8C(O)NR^8$—, CN, $NO_2$, $(R^8)_2N$—$C(NR^8)$—, $R^8C(O)$—, $R^8OC(O)$—, $N_3$, —$N(R^8)_2$, or $R^9OC(O)NR^8$—,
c) $C_1$–$C_6$ alkyl unsubstituted or substituted by unsubstituted or substituted aryl, unsubstituted or substituted heterocyclic, unsubstituted or substituted $C_3$–$C_6$ cycloalkyl, $C_2$–$C_6$ alkenyl, $C_2$–$C_6$ alkynyl, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)$—$NR^8$—;

$R^{2a}$, $R^{2b}$ and $R^3$ are independently selected from:
a) hydrogen,
b) $C_1$–$C_6$ alkyl unsubstituted or substituted by $C_2$–$C_6$ alkenyl, $R^8O$—, $R^9S(O)_m$—, $R^8C(O)NR^8$—, CN, $N_3$, $(R^8)_2N$—$C(NR^8)$—, $R^8C(O)$—, $R^8OC(O)$—, —$N(R^8)_2$, or $R^9OC(O)NR^8$—,
c) unsubstituted or substituted aryl, unsubstituted or substituted heterocycle, unsubstituted or substituted cycloalkyl, alkenyl, $R^8O$—, $R^9S(O)_m$—, $R^8C(O)$ $NR^8$—, CN, $NO_2$, $(R^8)_2N$—$C(NR^8)$—, $R^8C(O)$—, $R^8OC(O)$—, $N_3$, —$N(R^8)_2$, halogen or $R^9OC(O)NR^8$—, and
d) $C_1$–$C_6$ alkyl substituted with an unsubstituted or substituted group selected from aryl, heterocyclic and $C_3$–$C_{10}$ cycloalkyl;

$R^4$ and $R^5$ are independently selected from:
a) hydrogen, and

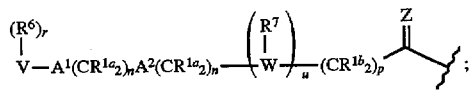

$R^6$ is independently selected from:
a) hydrogen,
b) unsubstituted or substituted aryl, unsubstituted or substituted heterocycle, unsubstituted or substituted $C_3$–$C_6$ cycloalkyl, $C_2$–$C_6$ alkenyl, $C_2$–$C_6$ alkynyl, $C_1$–$C_6$ perfluoroalkyl, F, Cl, Br, $R^8O$—, $R^9S(O)_m$—, $R^8C(O)NR^8$—, CN, $NO_2$, $R^8_2N$—$C(NR^8)$—, $R^8C(O)$—, $R^8OC(O)$—, $N_3$, —$N(R^8)_2$, or $R^9OC(O)NR^8$—, and
c) $C_1$–$C_6$ alkyl unsubstituted or substituted by unsubstituted or substituted aryl, unsubstituted or substituted heterocycle, unsubstituted or substituted $C_3$–$C_6$ cycloalkyl, $C_2$–$C_6$ alkenyl, $C_2$–$C_6$ alkynyl, $C_1$–$C_6$ perfluoroalkyl, F, Cl, Br, $R^8O$—, $R^9S(O)_m$—, $R^8C(O)NH$—, CN, $H_2N$—$C(NH)$—, $R^8C(O)$—, $R^8OC(O)$—, $N_3$, —$N(R^8)_2$, or $R^8OC(O)NH$—;

$R^7$ is selected from:
a) hydrogen,
b) $C_2$–$C_6$ alkenyl, $C_2$–$C_6$ alkynyl, $C_1$–$C_6$ perfluoroalkyl, F, Cl, Br, $R^8O$—, $R^9S(O)_m$—, $R^8C(O)NR^8$—, CN, $NO_2$, $(R^8)_2N$—$C$—$(NR^8)$—, $R^8C(O)$—, $R^8OC(O)$—, $N_3$, —$N(R^8)_2$, or $R^9OC(O)NR^8$—, and
c) $C_1$–$C_6$ alkyl unsubstituted or substituted by $C_1$–$C_6$ perfluoroalkyl, F, Cl, Br, $R^8O$—, $R^9S(O)_m$—, $R^8C(O)NR^8$—, CN, $(R^8)_2N$—$C(NR^8)$—, $R^8C(O)$—, $R^8OC(O)$—, $N_3$, —$N(R^8)_2$, or $R^9OC(O)NR^8$—;

$R^8$ is independently selected from hydrogen, $C_1$–$C_6$ alkyl, substituted or unsubstituted $C_1$–$C_6$ aralkyl and substituted or unsubstituted aryl;

$R^9$ is independently selected from $C_1$–$C_6$ alkyl and aryl;

$R^{10}$ is independently selected from hydrogen, $C_1$–$C_6$ alkyl, substituted or unsubstituted $C_1$–$C_6$ aralkyl and substituted or unsubstituted aryl;

$A^1$ and $A^2$ are independently selected from: a bond, —CH=CH—, —C≡C—, —C(O)—, —C(O)$NR^8$—, —$NR^8C(O)$—, O, —$N(R^8)$—, —$S(O)_2N(R^8)$—, —$N(R^8)S(O)_2$—, or $S(O)_m$;

V is selected from:
a) hydrogen,
b) heterocycle,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;

Y is selected from: a bond, —$C(R^{10})$=$C(R^{10})$—, —C≡C—, —C(O)—, —$C(R^{10})_2$—, —$C(OR^{10})$ $R^{10}$—, —$CN(R^{10})_2R^{10}$—, —$OC(R^{10})_2$—, —$NR^{10}C$ $(R^{10})_2$—, —$C(R^{10})_2O$—, —$C(R^{10})_2NR^{10}$—, —$C(O)$ $NR^{10}$—, —$NR^{10}C(O)$—, O, —$NC(O)R^{10}$—, —$NC(O)$ $OR^{10}$—, —$S(O)_2N(R^{10})$—, —$N(R^{10})S(O)_2$—, or $S(O)_m$;

Z is $H_2$ or O;

m is 0, 1 or 2;

n is 0, 1, 2, 3 or 4;

p is 0, 1, 2, 3 or 4;

r is 0 to 5, provided that r is 0 when V is hydrogen; and u is 0 or 1;

or the pharmaceutically acceptable salts thereof.

In a more preferred embodiment of this invention, the Ras farnesyl transferase inhibitors are illustrated by the Formula Ia:

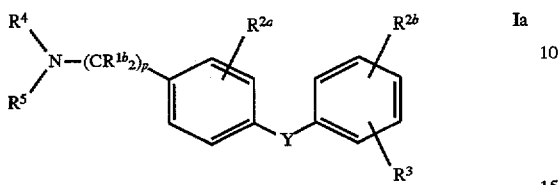

wherein:

$R^{1a}$ is independently selected from: hydrogen or $C_1$–$C_6$ alkyl;

$R^{1b}$ is independently selected from:
a) hydrogen,
b) unsubstituted or substituted aryl, unsubstituted or substituted heterocycle, unsubstituted or substituted $C_3$–$C_6$ cycloalkyl, $R^8O$—, —$(R^8)_2$ or $C_2$–$C_6$ alkenyl,
c) $C_1$–$C_6$ alkyl unsubstituted or substituted with 1 or 2 substituents selected from: unsubstituted or substituted aryl, unsubstituted or substituted heterocycle, unsubstituted or substituted $C_3$–$C_6$ cycloalkyl, $C_2$–$C_6$ alkenyl, $R^8O$—, and —$N(R^8)_2$;

$R^{2a}$ and $R^{2b}$ are independently selected from:
a) hydrogen,
b) $C_1$–$C_6$ alkyl unsubstituted or substituted by a substituent selected from: $R^8O$—, —$N(R^8)_2$, and $R^9S(O)_m$—,
c) substituted or unsubstituted aryl, and
d) halogen selected from F, I, Cl and Br;

$R^3$ is selected from:
a) hydrogen,
b) $C_1$–$C_6$ alkyl unsubstituted or substituted by a substituent selected from: $R^8O$—, —$N(R^8)_2$ and $R^9S(O)_m$—,
c) substituted or unsubstituted aryl,
d) halogen selected from F, I, Cl and Br, and
e) —$CO_2R^8$—;

$R^4$ and $R^5$ are independently selected from:
a) hydrogen, and

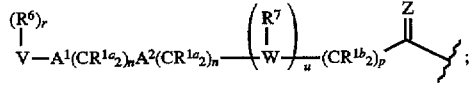

$R^6$ is selected from:
a) hydrogen,
b) substituted or unsubstituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and
c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, $R^8OC(O)$—, —$N(R^8)_2$, or $R^9OC(O)NR^8$—;

$R^7$ is selected from:
a) hydrogen,
b) $C_2$–$C_6$ alkenyl, $C_2$–$C_6$ alkynyl, $C_1$–$C_6$ perfluoroalkyl, F, Cl, $R^8O$—, $R^9S(O)_m$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and
c) $C_1$–$C_6$ alkyl unsubstituted or substituted by $C_1$–$C_6$ perfluoroalkyl, F, Cl, $R^8O$—, $R^9S(O)_m$—, $R^8C(O)NR^8$—, CN, $(R^8)_2N$—$C(NR^8)$—, $R^8C(O)$—, $R^8OC(O)$—, —$N(R^8)_2$, or $R^9OC(O)NR^8$—;

$R^8$ is independently selected from hydrogen, $C_1$–$C_6$ alkyl, substituted or unsubstituted $C_1$–$C_6$ aralkyl and substituted or unsubstituted aryl;

$R^9$ is independently selected from $C_1$–$C_6$ alkyl and aryl;

$R^{10}$ is independently selected from hydrogen, $C_1$–$C_3$ alkyl and benzyl;

$A^1$ and $A^2$ are independently selected from: a bond, —CH=CH—, —C≡C—, —C(O)—, —C(O)NR$^8$—, O, —N(R$^8$)—, or $S(O)_m$;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

W is a heterocycle selected from pyrrolidinyl, imidazolyl, imidazolinyl, pyridinyl, thiazolyl, pyridonyl, 2-oxopiperidinyl, indolyl, quinolinyl, or isoquinolinyl;

Y is selected from: —CH=CH—, —C≡C—, —C(O)—, —C(R$^{10}$)$_2$—, —C(OR$^{10}$)R$^{10}$—, —CN(R$^{10}$)$_2$R$^{10}$—, —OC(R$^{10}$)$_2$—, —NR$^{10}$C(R$^{10}$)$_2$—, —C(R$^{10}$)$_2$O—, —C(R$^{10}$)$_2$NR$^{10}$—, —C(O)NR$^{10}$—, —NR$^{10}$C(O)—, O, —NC(O)R$^{10}$—, —NC(O)OR$^{10}$—, —S(O)$_2$N(R$^{10}$)—, —N(R$^{10}$)S(O)$_2$—, or $S(O)_m$;

Z is $H_2$ or O;

m is 0, 1 or 2;

n is 0, 1, 2, 3 or 4;

p is 0, 1, 2, 3 or 4;

r is 0 to 5, provided that r is 0 when V is hydrogen; and u is 0 or 1;

or the pharmaceutically acceptable salts thereof.

In another preferred embodiment of this invention, the Ras farnesyl transferase inhibitors are illustrated by the Formula Ib:

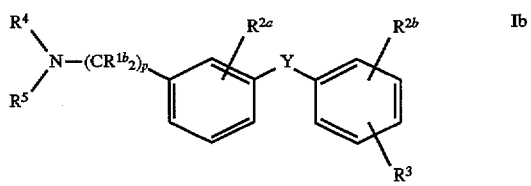

wherein:

$R^{1a}$ is independently selected from: hydrogen or $C_1$–$C_6$ alkyl;

$R^{1b}$ is independently selected from:
a) hydrogen,
b) unsubstituted or substituted aryl, unsubstituted or substituted heterocycle, unsubstituted or substituted $C_3$–$C_6$ cycloalkyl, $R^8O$—, —$N(R^8)_2$ or $C_2$–$C_6$ alkenyl,
c) $C_1$–$C_6$ alkyl unsubstituted or substituted with 1 or 2 substituents selected from: unsubstituted or substituted aryl, unsubstituted or substituted heterocycle, unsubstituted or substituted $C_3$–$C_6$ cycloalkyl, $C_2$–$C_6$ alkenyl, $R^8O$—, and —$N(R^8)_2$;

$R^{2a}$ and $R^{2b}$ are independently selected from:
  a) hydrogen,
  b) $C_1$–$C_6$ alkyl unsubstituted or substituted by a substituent selected from: $R^8O$—, —$N(R^8)_2$, and $R^9S(O)_m$—,
  c) substituted or unsubstituted aryl, and
  d) halogen selected from F, I, Cl and Br;

$R^3$ is selected from:
  a) hydrogen,
  b) $C_1$–$C_6$ alkyl unsubstituted or substituted by a substituent selected from: $R^8O$—, —$N(R^8)_2$ and $R^9S(O)_m$—,
  c) substituted or unsubstituted aryl,
  d) halogen selected from F, I, Cl and Br, and
  e) —$CO_2R^8$—;

$R^4$ and $R^5$ are independently selected from:
  a) hydrogen, and

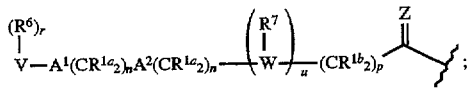

$R^6$ is selected from:
  a) hydrogen,
  b) substituted or unsubstituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and
  c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, $R^8OC(O)$—, —$N(R^8)_2$, or $R^9OC(O)NR^8$—;

$R^7$ is selected from:
  a) hydrogen,
  b) $C_2$–$C_6$ alkenyl, $C_2$–$C_6$ alkynyl, $C_1$–$C_6$ perfluoroalkyl, F, Cl, $R^8O$—, $R^9S(O)_m$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and
  c) $C_1$–$C_6$ alkyl unsubstituted or substituted by $C_1$–$C_6$ perfluoroalkyl, F, Cl, $R^8O$—, $R^9S(O)_m$—, $R^8C(O)NR^8$—, CN, $(R^8)_2N$—$C(NR^8)$—, $R^8C(O)$—, $R^8OC(O)$—, —$N(R^8)_2$, or $R^9OC(O)NR^8$—;

$R^8$ is independently selected from hydrogen, $C_1$–$C_6$ alkyl, substituted or unsubstituted $C_1$–$C_6$ aralkyl and substituted or unsubstituted aryl;

$R^9$ is independently selected from $C_1$–$C_6$ alkyl and aryl;

$R^{10}$ is independently selected from hydrogen, $C_1$–$C_3$ alkyl and benzyl;

$A^1$ and $A^2$ are independently selected from: a bond, —CH=CH—, —C≡C—, —C(O)—, —C(O)$NR^8$—, O, —$N(R^8)$—, or $S(O)_m$;

V is selected from:
  a) hydrogen,
  b) heterocycle selected from pyrrolidinyl, imidazolyl, pyridinyl, thiazolyl, pyridonyl, 2-oxopiperidinyl, indolyl, quinolinyl, isoquinolinyl, and thienyl,
  c) aryl,
  d) $C_1$–$C_{20}$ alkyl wherein from 0 to 4 carbon atoms are replaced with a a heteroatom selected from O, S, and N, and
  e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

W is a heterocycle selected from pyrrolidinyl, imidazolyl, imidazolinyl, pyridinyl, thiazolyl, pyridonyl, 2-oxopiperidinyl, indolyl, quinolinyl, or isoquinolinyl;

Y is selected from: —CH=CH—, —C≡C—, —C(O)—, —$C(R^{10})_2$—, —$C(OR^{10})R^{10}$—, —$CN(R^{10})_2R^{10}$—, —$OC(R^{10})_2$—, —$NR^{10}C(R^{10})_2$—, —$C(R^{10})_2O$—, —$C(R^{10})_2NR^{10}$—, —$C(O)NR^{10}$—, —$NR^{10}C(O)$—, O, —$NC(O)R^{10}$—, —$NC(O)OR^{10}$—, —$S(O)_2N(R^{10})$—, —$N(R^{10})S(O)_2$—, or $S(O)_m$;

Z is $H_2$ or O;

m is 0, 1 or 2;

n is 0, 1, 2, 3 or 4;

p is 0, 1, 2, 3 or 4;

r is 0 to 5, provided that r is 0 when V is hydrogen; and u is 0 or 1;

or the pharmaceutically acceptable salts thereof.

In another embodiment of this invention, the Ras farnesyl transferase inhibitors are illustrated by the Formula Ia:

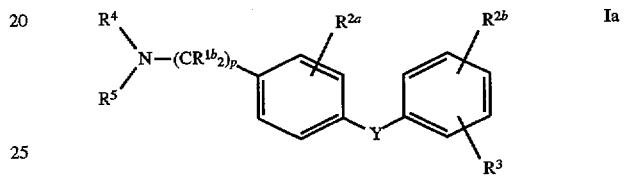

wherein:

$R^{1a}$ and $R^{1b}$ are independently selected from: hydrogen or $C_1$–$C_6$ alkyl;

$R^{2a}$ and $R^{2b}$ are independently selected from:
  a) hydrogen,
  b) $C_1$–$C_6$ alkyl unsubstituted or substituted by a substituent selected from: $R^8O$—, —$N(R^8)_2$, and $R^9S(O)_m$—,
  c) substituted or unsubstituted aryl, and
  d) halogen selected from F, I, Cl and Br;

$R^3$ is selected from:
  a) hydrogen,
  b) $C_1$–$C_6$ alkyl unsubstituted or substituted by a substituent selected from: $R^8O$—, —$N(R^8)_2$ and $R^9S(O)_m$—,
  c) substituted or unsubstituted aryl,
  d) halogen selected from F, I, Cl and Br, and
  e) —$CO_2R^8$—;

$R^4$ and $R^5$ are independently selected from:
  a) hydrogen, and
  b)

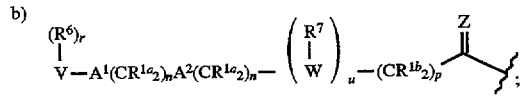

$R^6$ is selected from:
  a) hydrogen,
  b) substituted or unsubstituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and
  c) $C_1$–$C_6$ alkyl substituted by $C_1$–$C_6$ perfluoroalkyl, $R^8O$—, $R^8C(O)NR^8$—, $(R^8)_2N$—$C(NR^8)$—, $R^8C(O)$—, $R^8OC(O)$—, —$N(R^8)_2$, or $R^9OC(O)NR^8$—;

$R^7$ is selected from:
  a) hydrogen,
  b) $C_2$–$C_6$ alkenyl, $C_2$–$C_6$ alkynyl, $C_1$–$C_6$ perfluoroalkyl, F, Cl, $R^8O$—, $R^9S(O)_m$—, $R^8C(O)$ NR$^8$—, CN, NO$_2$, (R$^8$)$_2$N—C(NR$^8$)—, R$^8$C(O)—, R$^8$OC(O)—, —N(R$^8$)$_2$, or R$^9$OC(O)NR$^8$—, and c) C$_1$–C$_6$ alkyl unsubstituted or substituted by C$_1$–C$_6$ perfluoroalkyl, F, Cl, R$^8$O—, R$^9$S(O)$_m$—, R$^8$C(O)NR$^8$—, CN, (R$^8$)$_2$N—C(NR$^8$)—, R$^8$C(O)—, R$^8$OC(O)—, —N(R$^8$)$_2$, or R$^9$OC(O)NR$^8$—;

R$^8$ is independently selected from hydrogen, C$_1$–C$_6$ alkyl, substituted or unsubstituted C$_1$–C$_6$ aralkyl and substituted or unsubstituted aryl;

R$^9$ is independently selected from C$_1$–C$_6$ alkyl and aryl;

R$^{10}$ is independently selected from hydrogen, C$_1$–C$_3$ alkyl and benzyl;

A$^1$ and A$^2$ are independently selected from: a bond, —C(O)—, —C(O)NR$^8$—, —N(R$^8$)—, or S(O)$_m$;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl, and
c) aryl;

provided that V is not hydrogen if A$^1$ is S(O)$_m$ and V is not hydrogen if A$^1$ is a bond, n is 0 and A$^2$ is S(O)$_m$;

W is a heterocycle selected from imidazolyl, pyridinyl, quinolinyl, imidazolinyl or isoquinolinyl;

Y is selected from: —CH=CH—, —C≡C—, —C(O)—, —C(R$^{10}$)$_2$—, —C(OR$^{10}$)R$^{10}$—, —CN(R$^{10}$)$_2$R$^{10}$—, —OC(R$^{10}$)$_2$—, —NR$^{10}$C(R$^{10}$)$_2$—, —C(R$^{10}$)$_2$—, —C(R$^{10}$)$_2$NR$^{10}$—, —C(O)NR$^{10}$—, —NR$^{10}$C(O)—, O, —NC(O)R$^{10}$—, —NC(O)OR$^{10}$—, —S(O)$_2$N(R$^{10}$)—, —N(R$^{10}$)S(O)$_2$—, or S(O)$_m$;

Z is H$_2$ or O;
m is 0, 1 or 2;
n is 0, 1, 2, 3 or 4;
p is 0 or 1;
r is 0 to 5, provided that r is 0 when V is hydrogen; and
u is 0 or 1;
or the pharmaceutically acceptable salts thereof.

In a more preferred embodiment of this invention, the Ras farnesyl transferase inhibitors are illustrated by the Formula Ib:

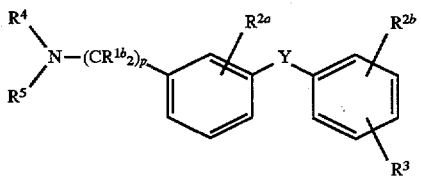

wherein:

R$^{1a}$ and R$^{1b}$ are independently selected from: hydrogen or C$_1$–C$_6$ alkyl;

R$^{2a}$ and R$^{2b}$ are independently selected from:
a) hydrogen,
b) C$_1$–C$_6$ alkyl unsubstituted or substituted by a substituent selected from: R$^8$O—, —N(R$^8$)$_2$, and R$^9$S(O)$_m$—,
c) substituted or unsubstituted aryl, and
d) halogen selected from F, I, Cl and Br;

R$^3$ is selected from:
a) hydrogen,
b) C$_1$–C$_6$ alkyl unsubstituted or substituted by a substituent elected from: R$^8$O—, —N(R$^8$)$_2$ and R$^9$S(O)$_m$—,
c) substituted or unsubstituted aryl,
d) halogen selected from F, I, Cl and Br, and
e) —CO$_2$R$^8$—;

R$^4$ and R$^5$ are independently selected from:
a) hydrogen, and $$(R^6)_r\ |\ V-A^1(CR^{1a}{}_2)_nA^2(CR^{1a}{}_2)_n-\left(W\!\!-\!\!\!\!\!\!\!\diagup\right)_u-(CR^{1b}{}_2)_p-\overset{Z}{\underset{}{C}}\diagup$$

R$^6$ is selected from:
a) hydrogen,
b) substituted or unsubstituted aryl, C$_1$–C$_6$ alkyl, C$_2$–C$_6$ alkenyl, C$_2$–C$_6$ alkynyl, C$_1$–C$_6$ perfluoroalkyl, F, Cl, R$^8$O—, R$^8$C(O)NR$^8$—, CN, NO$_2$, (R$^8$)$_2$N—C(NR$^8$)—, R$^8$C(O)—, R$^8$OC(O)—, —N(R$^8$)$_2$, or R$^9$OC(O)NR$^8$—, and
c) C$_1$–C$_6$ alkyl substituted by C$_1$–C$_6$ perfluoroalkyl, R$^8$O—, R$^8$C(O)NR$^8$—, (R$^8$)$_2$N—C(NR$^8$)—, R$^8$C(O)—, R$^8$OC(O)—, —N(R$^8$)$_2$, or R$^9$OC(O)NR$^8$—;

R$^7$ is selected from:
a) hydrogen,
b) C$_2$–C$_6$ alkenyl, C$_2$–C$_6$ alkynyl, C$_1$–C$_6$ perfluoroalkyl, F, Cl, R$^8$O—, R$^9$S(O)$_m$—, R$^8$C(O)NR$^8$—, CN, NO$_2$, (R$^8$)$_2$N—C(NR$^8$)—, R$^8$C(O)—, R$^8$OC(O)—, —N(R$^8$)$_2$, or R$^9$OC(O)NR$^8$—, and
c) C$_1$–C$_6$ alkyl unsubstituted or substituted by C$_1$–C$_6$ perfluoroalkyl, F, Cl, R$^8$O—, R$^9$S(O)$_m$—, R$^8$C(O)NR$^8$—, CN, (R$^8$)$_2$N—C(NR$^8$)—, R$^8$C(O)—, R$^8$OC(O)—, —N(R$^8$)$_2$, or R$^9$OC(O)NR$^8$—;

R$^8$ is independently selected from hydrogen, C$_1$–C$_6$ alkyl, substituted or unsubstituted C$_1$–C$_6$ aralkyl and substituted or unsubstituted aryl;

R$^9$ is independently selected from C$_1$–C$_6$ alkyl and aryl;

R$^{10}$ is independently selected from hydrogen, C$_1$–C$_3$ alkyl and benzyl;

A$^1$ and A$^2$ are independently selected from: a bond, —C(O)—, —C(O)NR$^8$—, —N(R$^8$)—, or S(O)$_m$;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl, and
c) aryl;

provided that V is not hydrogen if A$^1$ is S(O)$_m$ and V is not hydrogen if A$^1$ is a bond, n is 0 and A$^2$ is S(O)$_m$;

W is a heterocycle selected from imidazolyl, pyridinyl, quinolinyl, imidazolinyl or isoquinolinyl;

Y is selected from: —CH=CH—, —C≡C—, —C(O)—, —C(R$^{10}$)$_2$—, —C(OR$^{10}$)R$^{10}$—, —CN(R$^{10}$)$_2$R$^{10}$—, —OC(R$^{10}$)$_2$—, —NR$^{10}$C(R$^{10}$)$_2$—, —C(R$^{10}$)$_2$O—, —C(R$^{10}$)$_2$NR$^{10}$—, —C(O)NR$^{10}$—, —NR$^{10}$C(O)—, O, —NC(O)R$^{10}$—, —NC(O)OR$^{10}$—, —S(O)$_2$N(R$^{10}$)—, —N(R$^{10}$)S(O)$_2$—, or S(O)$_m$;

Z is H$_2$ or O;
m is 0, 1 or 2;
n is 0, 1, 2, 3 or 4;
p is 0 or 1;
r is 0 to 5, provided that r is 0 when V is hydrogen; and
u is 0 or 1;
or the pharmaceutically acceptable salts thereof.

Specific examples of compounds of this invention are as follows:

N,N-bis(4-Imidazolemethyl)amino-3-[(3-carboxyphenyl)oxy]benzene

N,N-bis(4-Imidazolemethyl)amino-4-[(3-carboxyphenyl)
oxy]benzene

N,N-bis(4-Imidazolemethyl)amino-3-[(3-
carbomethoxyphenyl)oxy]benzene

N,N-bis(4-Imidazolemethyl)amino-4-[(3-
carbomethoxyphenyl)oxy]benzene

N-(4-Imidazolemethyl)-N-(4-nitrobenzyl)aminomethyl-
3-[(3-carboxyphenyl)oxy]benzene N-(4-Imidazolemethyl)-N-(4-nitrobenzyl)aminomethyl-
3-[(3-carbomethoxyphenyl)oxy]benzene N-(4-Imidazolemethyl)-N-(4-nitrobenzyl)amino-3-
(phenoxy)benzene N-(4-Imidazolemethyl)-N-(4-nitrobenzyl)amino-4-
(phenoxy)benzene N-(4-Imidazolemethyl)-N-(4-nitrobenzyl)amino-4-
(phenylthio)benzene N-Butyl-N-[1-(4-cyanobenzyl)-5-imidazolemethyl]
amino-4-(phenoxy)benzene N-[1-(4-Cyanobenzyl)-5-imidazolemethyl]amino-4-
(phenoxy)benzene N-(4-Imidazolemethyl)amino-3-[(3-carboxyphenyl)oxy]
benzene 1-[N-(1-(4-cyanobenzyl)-5-imidazolylmethyl)-N-(4-
cyanobenzyl)amino]-4-(phenoxy)benzene (±)-4-[(4-imidazolylmethyl)amino]pentyl-1-(phenoxy)
benzene 1-[(N-(1-(4-cyanobenzyl)-5-imidazolylmethyl)-N-(n-
butyl)amino)methyl]-4-(phenoxy)benzene 4-[N-(1-(4-cyanobenzyl)-5-imidazolylmethyl)-N-(n-
butyl)amino]-1-(phenylthio)benzene (±)-4-[N-(1-(4-cyanobenzyl)-4-imidazolylmethyl)-N-(n-
butyl)amino]-1-(phenylsulfinyl)benzene 3-[N-(4-imidazolylmethyl)-N-(n-butyl)amino]-N-
(phenyl)benzenesulfonamide and 1-[N-(1-(4-cyanobenzyl)-5-imidazolylmethyl)amino]-3-
methoxy-4-phenylbenzene or the pharmaceutically acceptable salts or optical isomers
thereof.

Particular examples of the compounds of the invention
are:

N-(4-Imidazolemethyl)-N-(4-nitrobenzyl)amino-3-(phenoxy)benzene

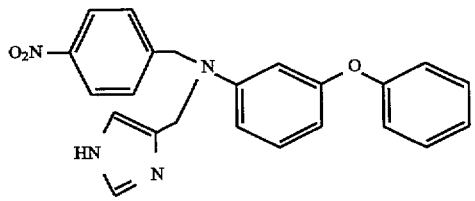

N-(4-Imidazolemethyl)-N-(4-nitrobenzyl)aminomethyl-3-[(3-
carbomethoxyphenyl)oxy[benzene

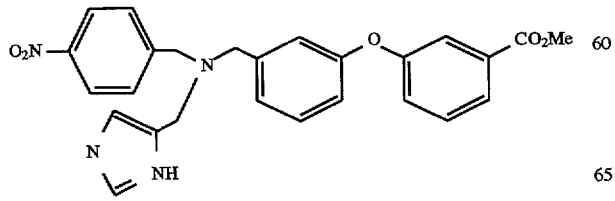

-continued

N-(4-Imidazolemethyl)amino-3-[(3-carboxyphenyl)oxy]benzene

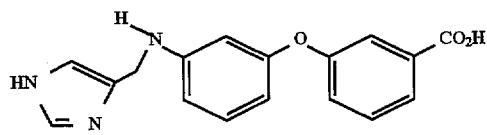

N,N-bis(4-Imidazolemethyl)amino-4-[(3-carbomethoxyphenyl)-
oxy]benzene

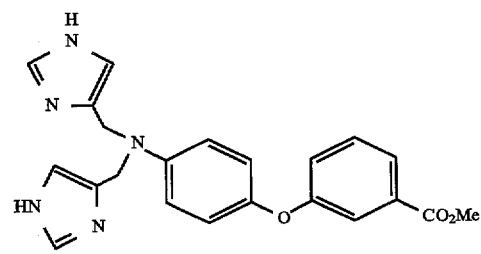

N-Butyl-N-[1-(4-cyanobenzyl)-5-imidazolemethyl]amino-4-
(phenoxy)benzene

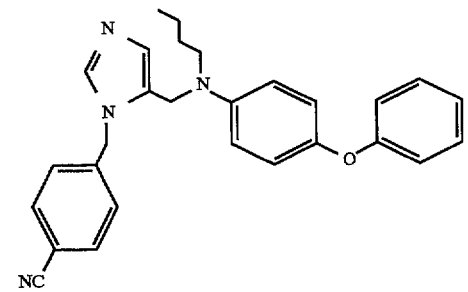

1-[N-(1-(4-cyanobenzyl)-5-imidazolylmethyl)-N-(4-cyanobenzyl)amino]-
4-(phenoxy)benzene

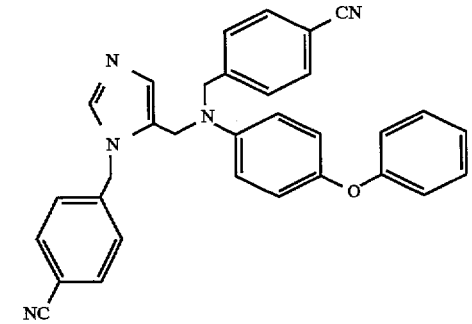

(±)-4-[N-(1-(4-cyanobenzyl)-4-imidazolylmethyl)-N-(n-butyl)amino]-1-
(phenylsulfinyl)benzene

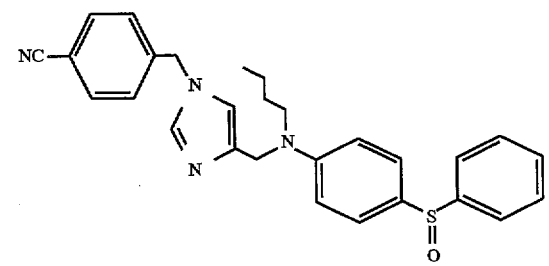

-continued

1-[N-(1-(4-cyanobenzyl)-5-imidazolylmethyl)amino]-3-methoxy-4-phenylbenzene

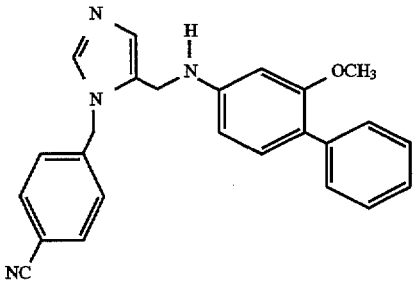

or the pharmaceutically acceptable salts or optical isomers thereof.

The compounds of the present invention may have asymmetric centers and occur as racemates, racemic mixtures, and as individual diastereomers, with all possible isomers, including optical isomers, being included in the present invention.

As used herein, "alkyl" is intended to include both branched and straight-chain saturated aliphatic hydrocarbon groups having the specified number of carbon atoms.

As used herein, "cycloalkyl" is intended to include non-aromatic cyclic hydrocarbon groups having the specified number of carbon atoms. Examples of cycloalkyl groups include cyclopropyl, cyclobutyl, cyclopentyl, cyclohexyl and the like.

"Alkenyl" groups include those groups having the specified number of carbon atoms and having one or several double bonds. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like.

As used herein, "aryl" is intended to include any stable monocyclic, bicyclic or tricyclic carbon ring(s) of up to 7 members in each ring, wherein at least one ring is aromatic. Examples of aryl groups include phenyl, naphthyl, anthracenyl, biphenyl, tetrahydronaphthyl, indanyl, phenanthrenyl and the like.

As used herein, "aralkyl" is intended to mean any stable monocyclic, bicyclic or tricyclic carbon ring of up to 7 members in each ring, wherein at least one ring is aromatic, attached to the rest of the molecule via a straight or branched-chain saturated aliphatic hydrocarbon group having the specified number of carbon atoms. Examples of such aralkyl elements include benzyl, phenylethyl, naphthylmethyl, naphthylethyl, tetrahydronaphthylmethyl, indanylmethyl, biphenylmethyl and the like.

The term heterocycle or heterocyclic, as used herein, represents a stable 5- to 7-membered monocyclic or stable 8- to 11-membered bicyclic or stable 11–15 membered tricyclic heterocycle ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothio-pyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, 2-oxopiperazinyl, 2-oxopiperidinyl, 2-oxopyrrolidinyl, piperidyl, piperazinyl, pyridyl, pyridyl N-oxide, pyridonyl, pyrazinyl, pyrazolidinyl, pyrazolyl, pyrimidinyl, pyrrolidinyl, pyrrolyl, quinazolinyl, quinolinyl, quinolinyl N-oxide, quinoxalinyl, tetrahydrofuryl, tetrahydroisoquinolinyl, tetrahydro-quinolinyl, thiamorpholinyl, thiamorpholinyl sulfoxide, thiazolyl, thiazolinyl, thienofuryl, thienothienyl, and thienyl. It is understood that the term heterocycle does not include tetrazolyl.

As used herein, the terms "substituted aryl", "substituted heterocycle" and "substituted cycloalkyl" are intended to include the cyclic group which is substituted with 1 or 2 substitutents selected from the group which includes but is not limited to F, Cl, Br, $CF_3$, $NH_2$, $N(C_1-C_6$ alkyl$)_2$, $NO_2$, CN, $(C_1-C_6$ alkyl)O—, —OH, $(C_1-C_6$ alkyl)S(O)$_m$—, $(C_1-C_6$ alkyl)C(O)NH—, $H_2N$—C(NH)—, $(C_1-C_6$ alkyl)C(O)—, $(C_1-C_6$ alkyl)OC(O)—, $N_3$,$(C_1-C_6$ alkyl)OC(O)NH—, phenyl, pyridyl, imidazolyl, oxazolyl, isoxazolyl, thiazolyl, thienyl, furyl, isothiazolyl and $C_1-C_{20}$ alkyl.

Preferably, $R^{1a}$ and $R^{1b}$ are independently selected from: hydrogen, —N(R$^8$)$_2$, R$^8$C(O)NR$^8$— or unsubstituted or substituted $C_1-C_6$ alkyl wherein the substituent on the substituted $C_1-C_6$ alkyl is selected from unsubstituted or substituted phenyl, —N(R$^8$)$_2$, R$^8$O— and R$^8$C(O)NR$^8$—. More preferably, $R^{1a}$ and $R^{1b}$ are independently selected from: hydrogen or unsubstituted or substituted $C_1-C_6$ alkyl.

Preferably, $R^{2a}$ and $R^{2b}$ are independently selected from: H, unsubstituted or substituted $C_1-C_6$ alkyl, R$^8$O— and halogen.

Preferably, $R^3$ is selected from: hydrogen, $C_1-C_6$ alkyl and —CO$_2$R$^8$. More preferably, $R^3$ is hydrogen.

Preferably, at least one of $R^4$ and $R^5$ is not hydrogen.

Preferably, $R^7$ is hydrogen or methyl. Most preferably, $R^7$ is hydrogen.

Preferably, $R^8$ is selected from H, $C_1-C_6$ alkyl and benzyl.

Preferably, $A^1$ and $A^2$ are independently selected from: a bond, —C(O)NR$^8$—, —NR$^8$C(O)—, O, —N(R$^8$)—, —S(O)$_2$N(R$^8$)— and —N(R$^8$)S(O)$_2$—.

Preferably, V is selected from hydrogen, heterocycle and aryl. More preferably, V is phenyl.

Preferable, W is selected from imidazolinyl, imidazolyl, oxazolyl, pyrazolyl, pyyrolidinyl, thiazolyl and pyridyl. More preferably, W is selected from imidazolyl and pyridyl.

Preferably, Y is a bond, —C(O)—, —C(R$^{10}$)$_2$—, —OC(R$^{10}$)$_2$—, —NR$^{10}$C(R$^{10}$)$_2$—, —C(R$^{10}$)$_2$O—, —C(R$^{10}$)$_2$NR$^{10}$—, —C(O)NR$^{10}$—, —NR$^{10}$C(O)—, O, —S(O)$_2$N(R$^{10}$)—, —N(R$^{10}$)S(O)$_2$—, or S(O)$_m$.

Preferably, n and p are independently 0, 1, or 2.

Preferably r is 1, 2 or 3.

Preferably u is 1.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

It is intended that the definition of any substituent or variable (e.g., $R^{1a}$, $R^8$, n, etc.) at a particular location in a molecule be independent of its definitions elsewhere in that molecule. Thus, —$N(R^8)_2$ represents —NHH, —$NHCH_3$, —$NHC_2H_5$, etc. It is understood that substituents and substitution patterns on the compounds of the instant invention can be selected by one of ordinary skill in the art to provide compounds that are chemically stable and that can be readily synthesized by techniques known in the art as well as those methods set forth below.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

The compounds of the invention can be synthesized from readily available starting materials by synthetic techniques well known in the art, and the additional methods described below.

Abbreviations used in the description of the chemistry and in the Examples that follow are:

| | |
|---|---|
| $Ac_2O$ | Acetic anhydride; |
| Boc | t-Butoxycarbonyl; |
| DBU | 1,8-diazabicyclo[5.4.0]undec-7-ene; |
| DMAP | 4-Dimethylaminopyridine; |
| DME | 1,2-Dimethoxyethane; |
| DMEM | Dulbecco's Minimal Essential Medium; |
| DMF | Dimethylformamide; |
| DMSO | Dimethylsulfoxide; |
| EDC | 1-(3-dimethylaminopropyl)-3-ethyl-carbodiimide-hydrochloride; |
| HOAc | Acetic acid; |
| HOBT | 1-Hydroxybenzotriazole hydrate; |
| $Et_3N$ | Triethylamine; |
| EtOAc | Ethyl acetate; |
| FAB | Fast atom bombardment; |
| HOOBT | 3-Hydroxy-1,2,2-benzotriazin-4(3H)-one; |
| HPLC | High-performance liquid chromatography; |
| MCPBA | m-Chloroperoxybenzoic acid; |
| MsCl | Methanesulfonyl chloride; |
| NaHMDS | Sodium bis(trimethylsilyl)amide; |
| Py | Pyridine; |
| TCA | Trichloroacetic acid; |
| $Tf_2NPh$ | N-Trifluoromethanesulfonamide; |
| TFA | Trifluoroacetic acid; |
| THF | Tetrahydrofuran. |

Compounds of this invention are prepared by employing the reactions shown in the following Reaction Schemes, in addition to other standard manipulations such as ester hydrolysis, cleavage of protecting groups, etc., as may be known in the literature or exemplified in the experimental procedures. Some key reactions utilized to form the aminodiphenyl moiety of the instant compounds are shown.

These reactions may be employed in a linear sequence to provide the compounds of the invention or they may be used to synthesize fragments which are subsequently joined by the alkylation reactions described in the Reaction Schemes.

Reaction Schemes A–P describe the preparation of appropriately substituted aniline intermediates that may be further functionalized by the methods described in Reaction Schemes Q–Y to provide the compounds of the instant invention.

Reaction Schemes A–D illustrate use of Ullman reactions to provide diphenyl ethers, amines and sulfides from readily available fully substituted phenols/thiophenols/anilines and aryl halides. In such syntheses, the desired amine moiety is typically masked as a nitro group which is subsequently reduced by techniques well known in the art. An alternative synthesis of the diphenyl ethers which employs para-nitro fluorobenzene is shown in Reaction Scheme E.

Reaction Scheme F illustrates standard acid-amine coupling to provide the fully substituted N-phenylbenzamides. Reaction Scheme G illustrates formation of the aminomethyl spacer via a reductive amination of a suitably substituted benzaldehyde.

Reaction Scheme H illustrates coupling of suitably substituted anilines with readily available phenylsulfonyl chlorides. Access to aminobenzophenones is illustrated in Reaction Scheme I, which also illustrates the reduction of the carbonyl to provide the unsubstituted methyl spacer. An alternative method of forming the benzophenone intermediates is illustrated in Reaction Scheme J. Also shown in Reaction Scheme J is reductive amination of the resulting carbonyl to provide the amine substituted methyl spacer. Another method of forming the benzophenone intermediates, illustrated in Reaction Scheme K, is a Stille reaction with an aryl stannane.

Reaction Schemes L and M illustrate palladium mediated formation of olefin and acetylene spacer units. Reaction Scheme N illustrates formation of an appropriately substituted benzyl ether. Reaction Scheme P illustrates the use of the Claisen rearrangement to provide methyl spacers having substituents such as a vinyl group which can be further functionalized.

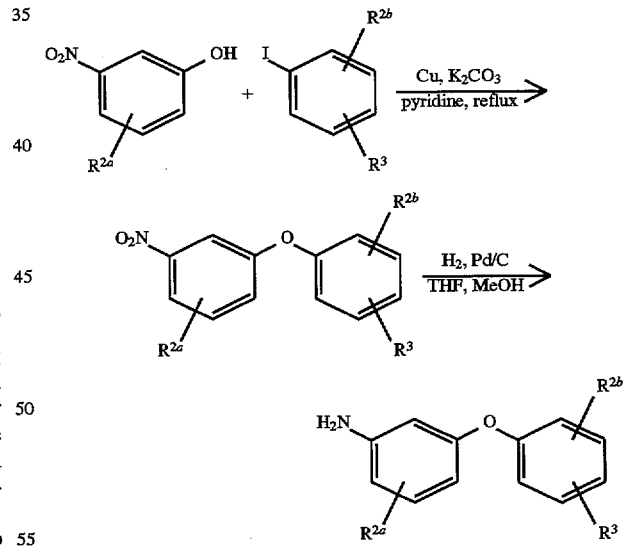

REACTION SCHEME A

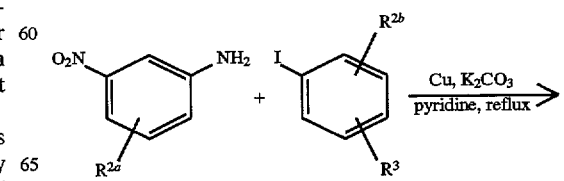

REACTION SCHEME B

REACTION SCHEME B -continued
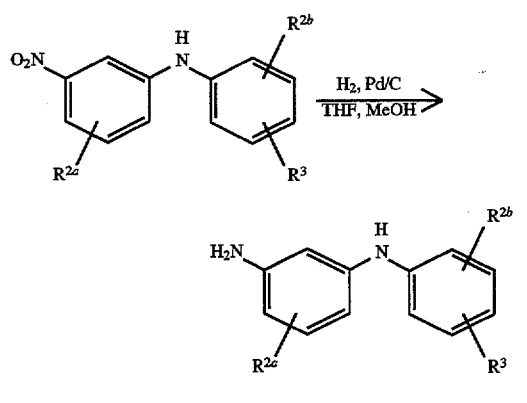
REACTION SCHEME C
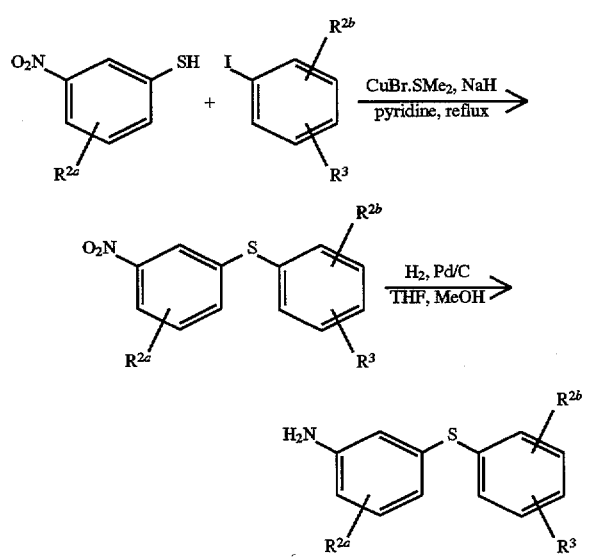
REACTION SCHEME D
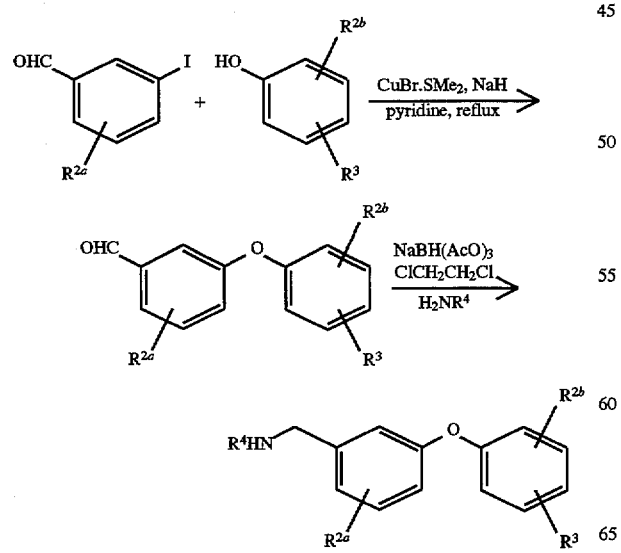
REACTION SCHEME E
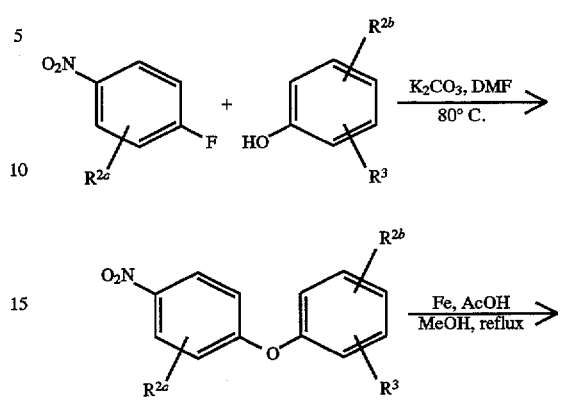
REACTION SCHEME F
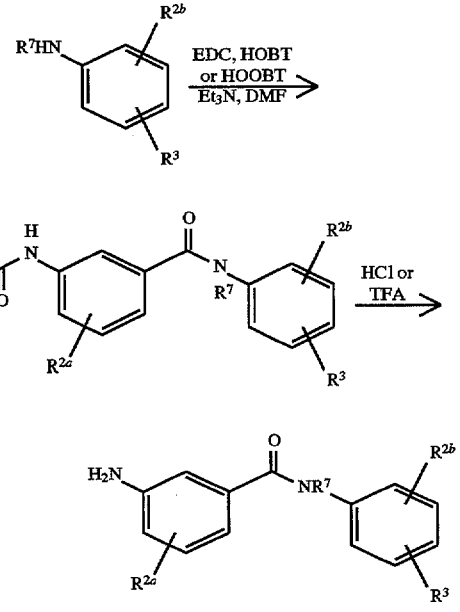

5,710,171
19
REACTION SCHEME G
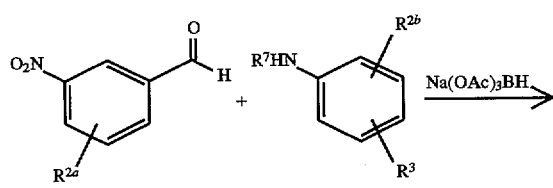
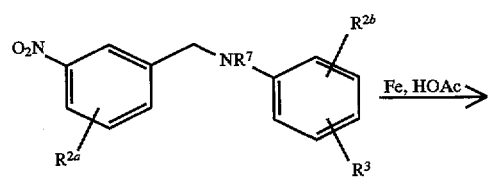
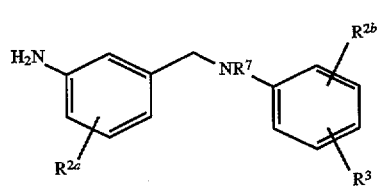
REACTION SCHEME H
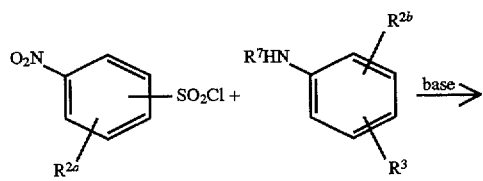
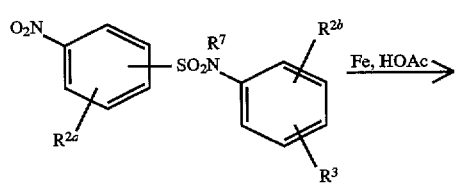
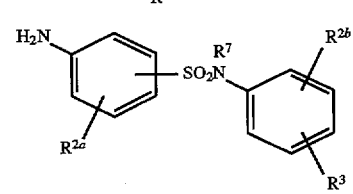
REACTION SCHEME I
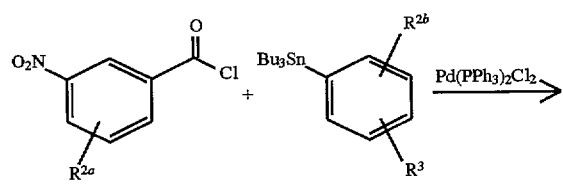
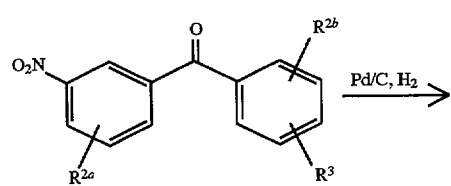
20
-continued
REACTION SCHEME I
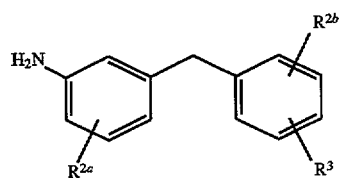
REACTION SCHEME J
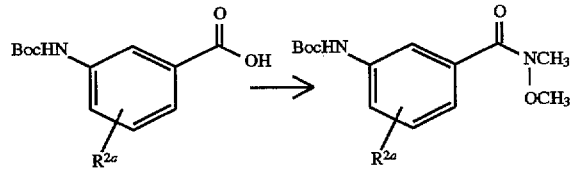
MgBrPh($R^{2a}$)($R^3$)
or
LiPh($R^{2a}$)($R^3$)
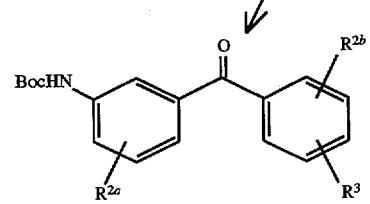
HN($R^8$)$_2$
NaBH(OAc)$_3$
ClCH$_2$CH$_2$Cl
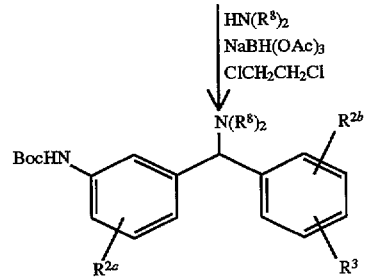
HCl or TFA
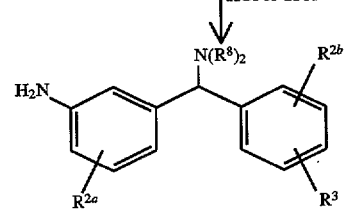
REACTION SCHEME K
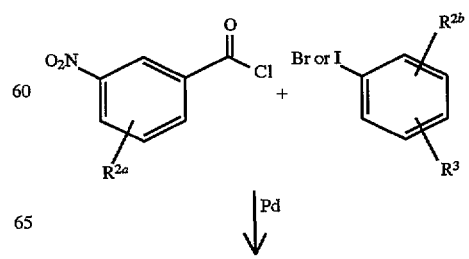
Pd

REACTION SCHEME K
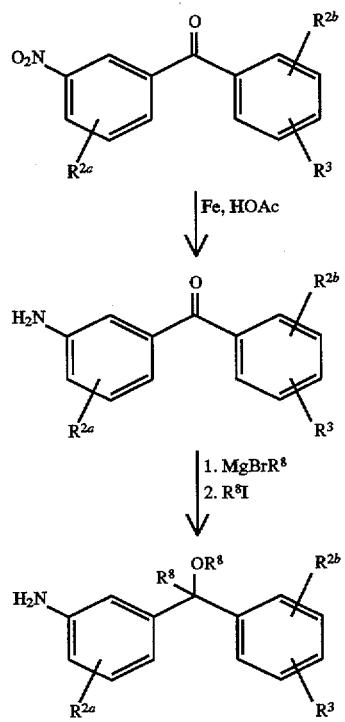
REACTION SCHEME L
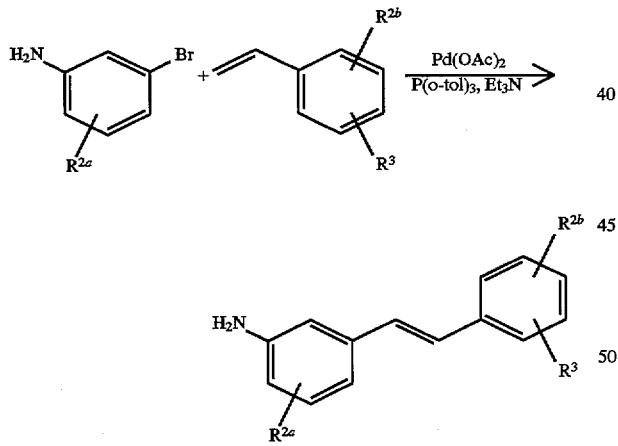
REACTION SCHEME M
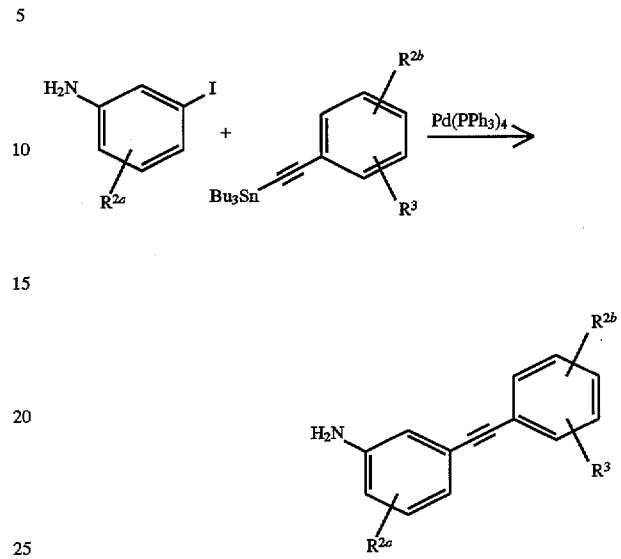
REACTION SCHEME N
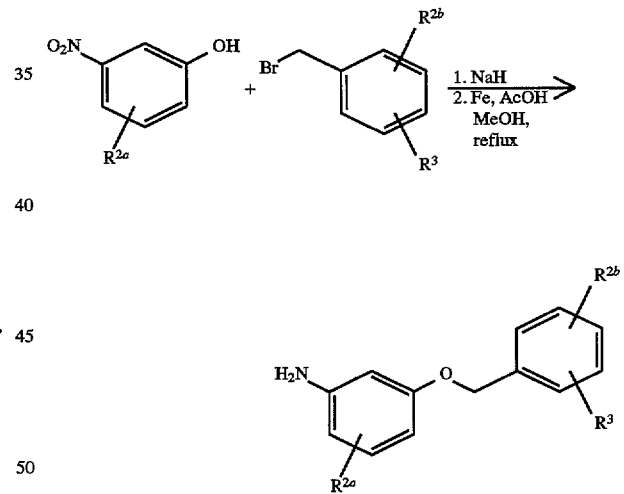

REACTION SCHEME P

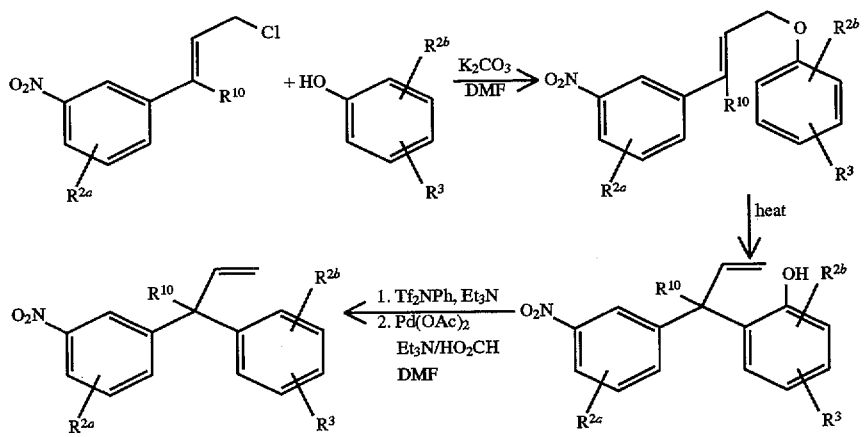

Reaction Schemes Q–Y illustrate reactions wherein the non-sulfhydryl-containing moiety(ies) of the compounds of the instant invention is attached to the aminodiphenyl subunit to provide the instant compounds.

The intermediates whose synthesis are illustrated in Reaction Schemes A–P hereinabove, can be reductively alkylated with a variety of aldehydes, as shown in Reaction Scheme Q. The aldehydes can be prepared by standard procedures, such as that described by O. P. Goel, U. Krolls, M. Stier and S. Kesten in *Organic Syntheses*, 1988, 67, 69–75, from the appropriate amino acid (Reaction Scheme Q). The reductive alkylation can be accomplished at pH 5–7 with a variety of reducing agents, such as sodium triacetoxyborohydride or sodium cyanoborohydride in a solvent such as dichloroethane, methanol or dimethylformamide. The product II can be deprotected with trifluoroacetic acid in methylene chloride to give the final compounds III. The final product III is isolated in the salt form, for example, as a trifluoroacetate, hydrochloride or acetate salt, among others. The product diamine III can further be selectively protected to obtain IV, which can subsequently be reductively alkylated with a second aldehyde to obtain V. Removal of the protecting group, and conversion to cyclized products such as the dihydroimidazole VII can be accomplished by literature procedures.

Alternatively, the aminodiphenyl subunit can be reductively alkylated with other aldehydes such as 1-trityl-4-carboxaldehyde or 1-trityl-4-imidazolylacetaldehyde, to give products such as VIII (Reaction Scheme R). The trityl protecting group can be removed from VIII to give IX, or alternatively, VIII can first be treated with an alkyl halide then subsequently deprotected to give the alkylated imidazole X. Alternatively, the aminomethylbenzamide subunit can be acylated or sulfonylated by standard techniques.

The imidazole acetic acid XI can be converted to the acetate XIII by standard procedures, and XIII can be first reacted with an alkyl halide, then treated with refluxing methanol to provide the regiospecifically alkylated imidazole acetic acid ester XIV. Hydrolysis and reaction with the aminodiphenyl subunit in the presence of condensing reagents such as 1-(3-dimethylaminopropyl)-3-ethylcarbodiimide (EDC) leads to acylated products such as XV.

If the aminodiphenyl subunit is reductively alkylated with an aldehyde which also has a protected hydroxyl group, such as XVI in Reaction Scheme T, the protecting groups can be subsequently removed to unmask the hydroxyl group (Reaction Schemes T, U). The alcohol can be oxidized under standard conditions to e.g. an aldehyde, which can then be reacted with a variety of organometallic reagents such as Grignard reagents, to obtain secondary alcohols such as XX. In addition, the fully deprotected amino alcohol XXI can be reductively alkylated (under conditions described previously) with a variety of aldehydes to obtain secondary amines, such as XXII (Reaction Scheme V), or tertiary amines.

The Boc protected amino alcohol XVIII can also be utilized to synthesize 2-aziridinylmethylaminodiphenyls such as XXIII (Reaction Scheme W). Treating XVIII with 1,1'-sulfonyldiimidazole and sodium hydride in a solvent such as dimethylformamide led to the formation of aziridine XXIII. The aziridine reacted in the presence of a nucleophile, such as a thiol, in the presence of base to yield the ring-opened product XXIV.

In addition, the aminodiphenyl subunit can be reacted with aldehydes derived from amino acids such as O-alkylated tyrosines, according to standard procedures, to obtain compounds such as XXX, as shown in Reaction Scheme X. When R' is an aryl group, XXX can first be hydrogenated to unmask the phenol, and the amine group deprotected with acid to produce XXXI. Alternatively, the amine protecting group in XXX can be removed, and O-alkylated phenolic amines such as XXXII produced.

Reaction Scheme Y illustrates a one pot synthesis of an instant compound wherein the N-terminus nitrogen is substituted with two different non-sulfhydryl-containing moieties. Thus, the aminodiphenyl subunit is treated with one equivalent of an appropriate aldehyde and, after the reductive adduct has been formed, the in situ intermediate is treated with an equivalent of a different aldehyde.

Reaction Schemes Z–CC illustrate syntheses of suitably substituted aldehydes useful in the syntheses of the instant compounds wherein the variable W is present as a pyridyl moiety. Similar synthetic strategies for preparing alkanols that incorporate other heterocyclic moieties for variable W are also well known in the art.

REACTION SCHEME Q
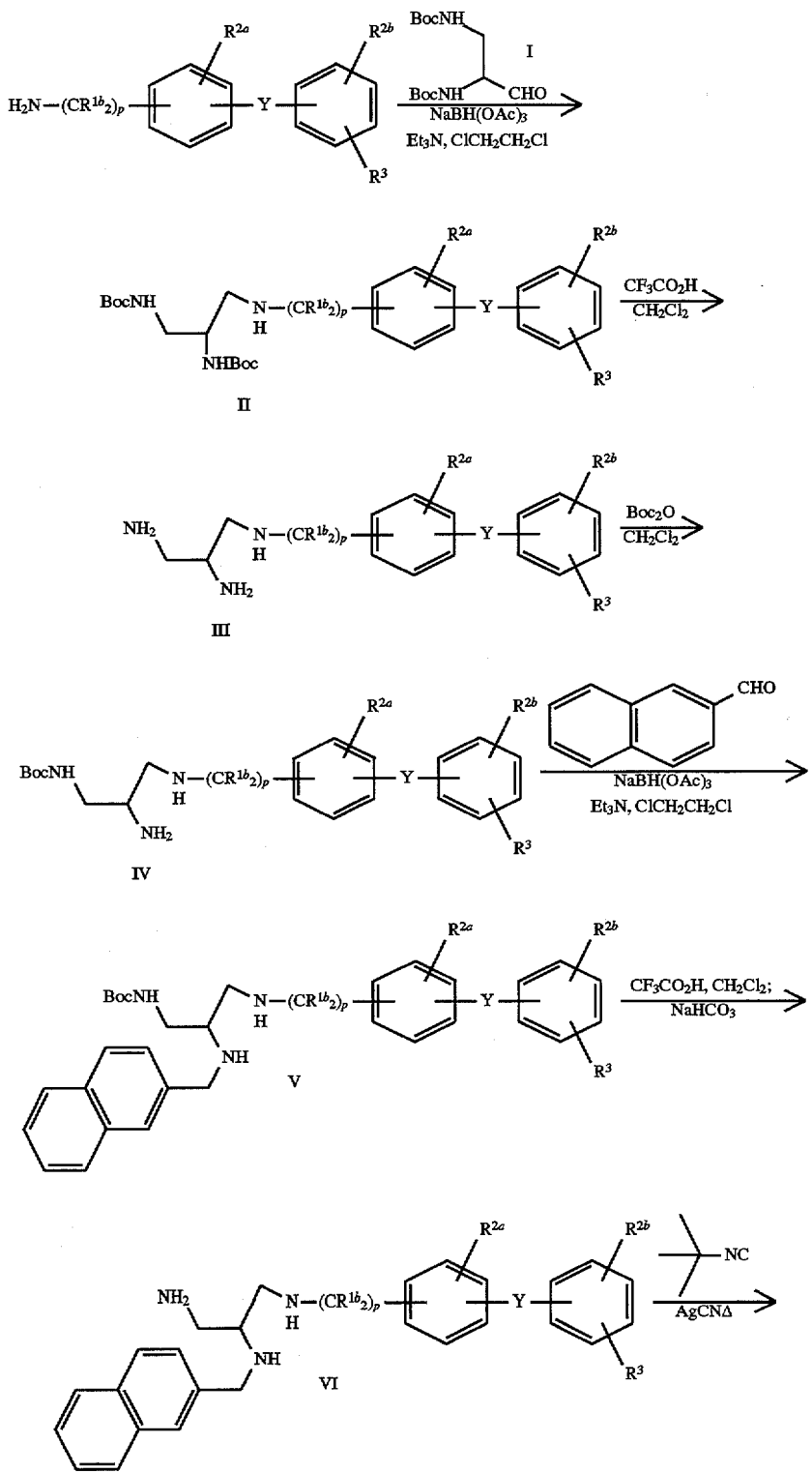

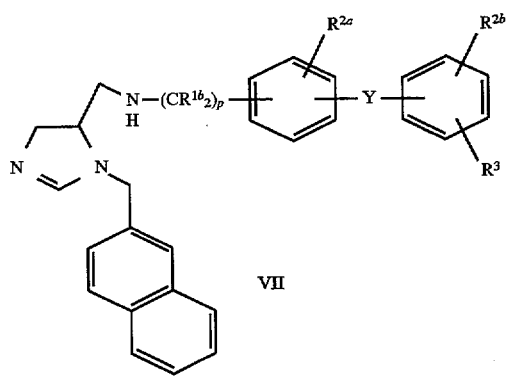
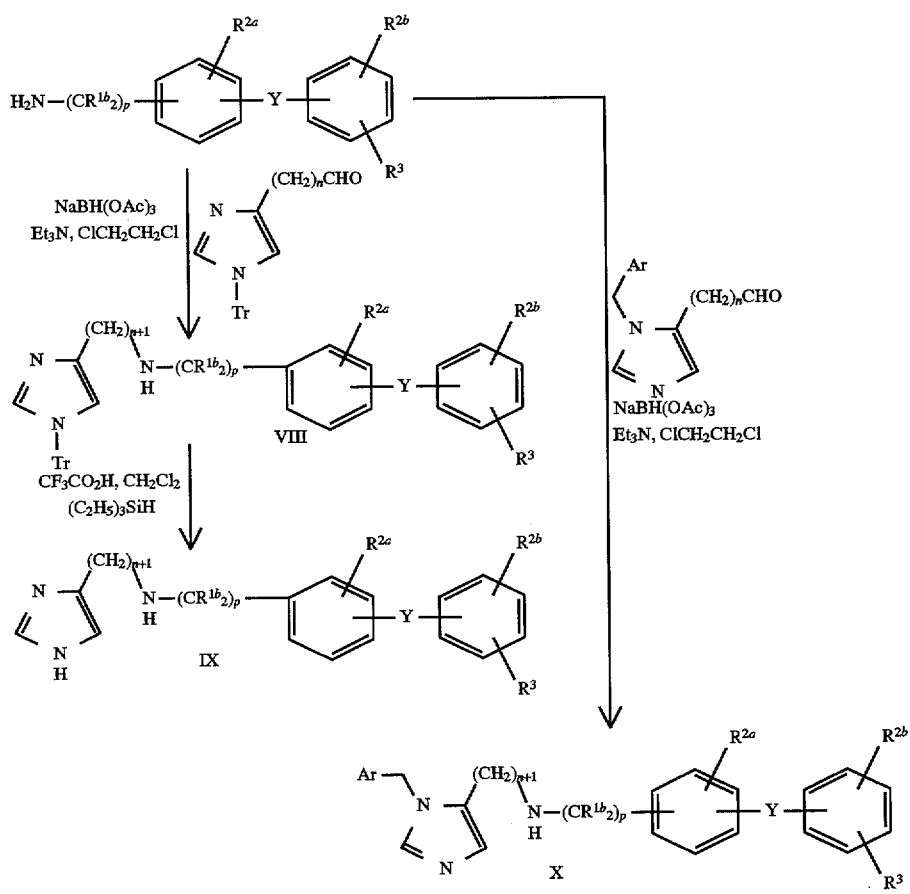
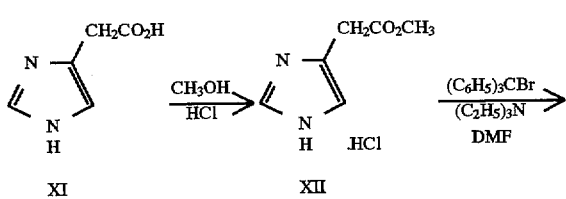
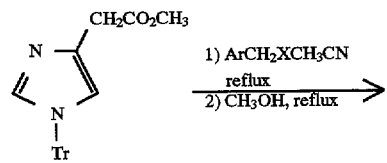

REACTION SCHEME S
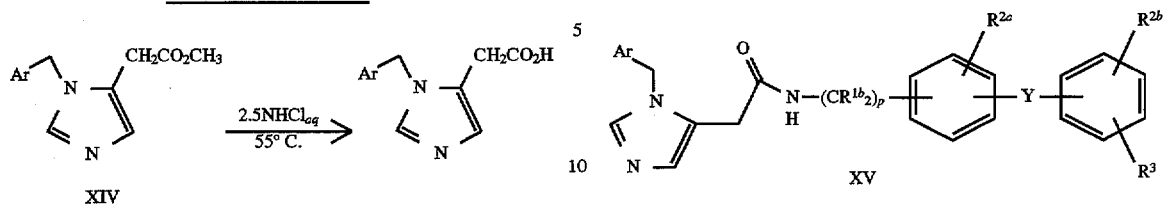
REACTION SCHEME T
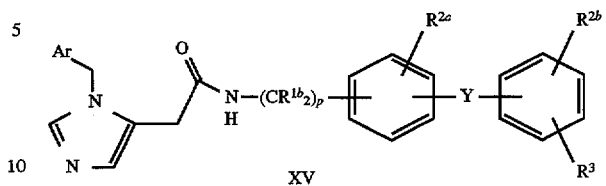
REACTION SCHEME T
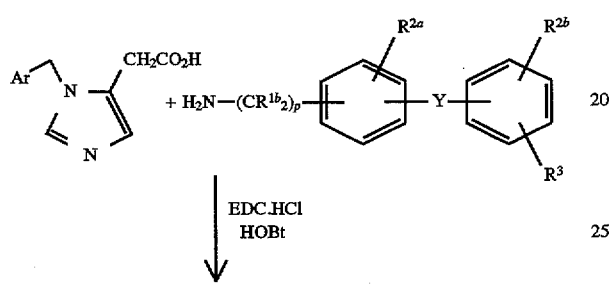
REACTION SCHEME U
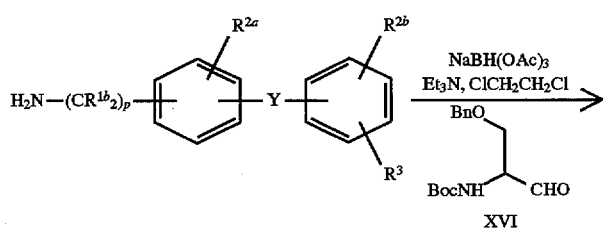
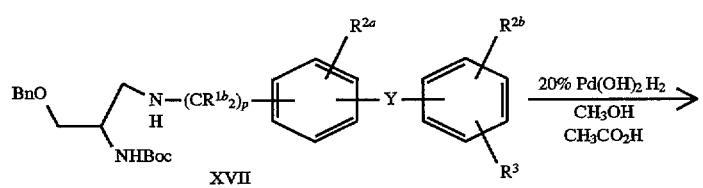
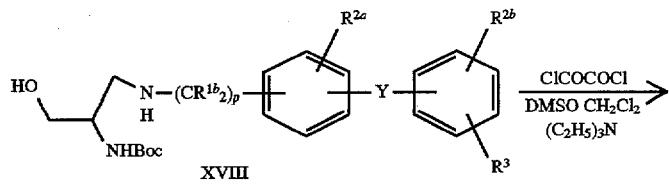
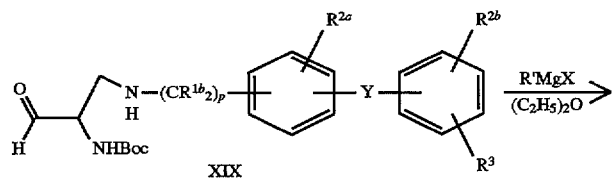

-continued
REACTION SCHEME U
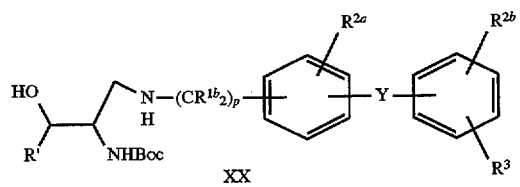
XX
REACTION SCHEME V
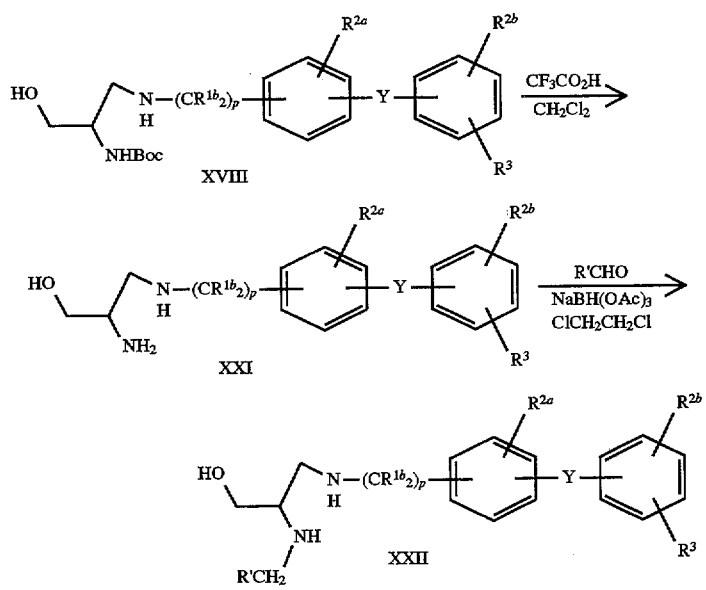
REACTION SCHEME W
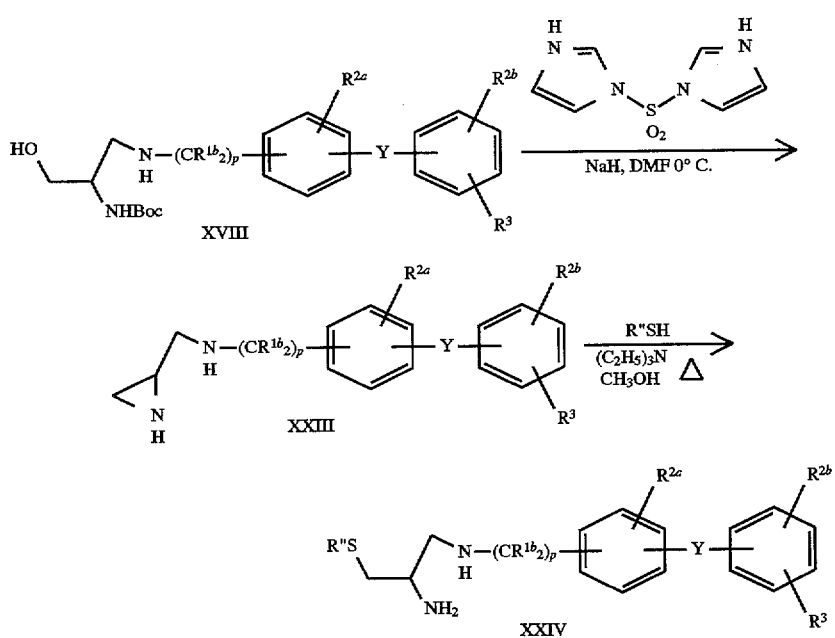

REACTION SCHEME X
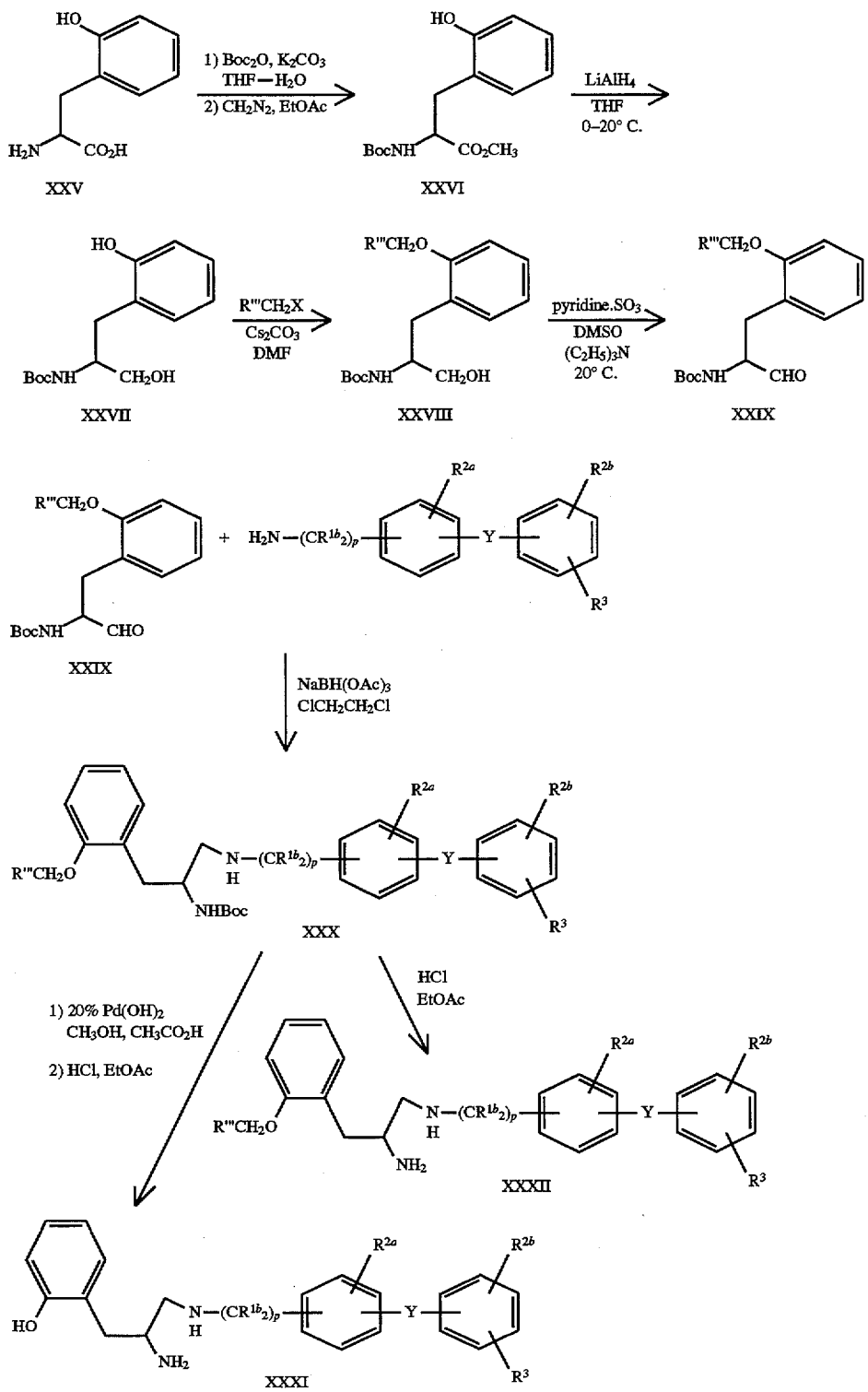

REACTION SCHEME Y
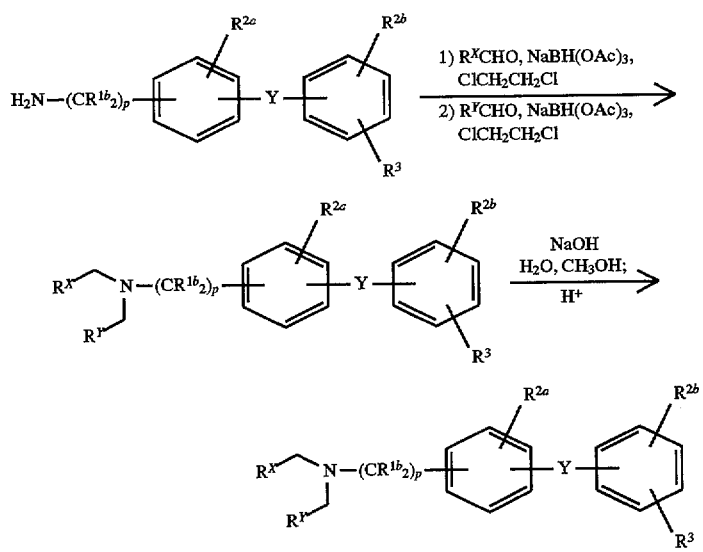
wherein, in the above Reaction Schemes, R' is $R^{1a}$; R" is $(R^6)_r$—V—$A^1$—$(CR^{1a})_n$—; R'" is selected such that R'"$CH_2$— is $R^8$; and $R^x$ and $R^y$ are selected such that $R^x CH_2$— and $R^y CH_2$— are either $R^4$ or $R^5$.
REACTION SCHEME Z
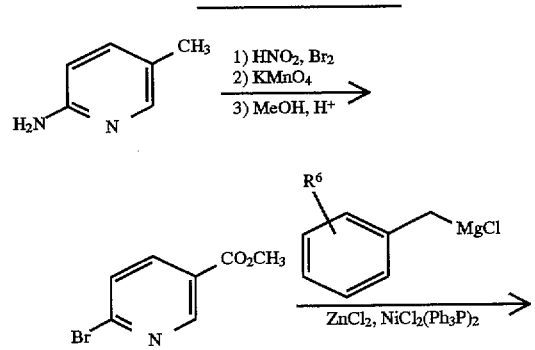
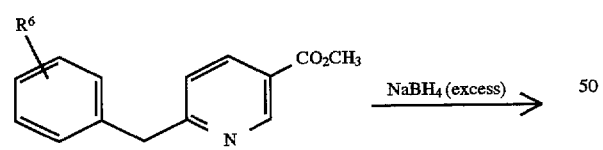
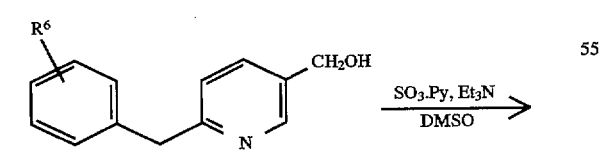
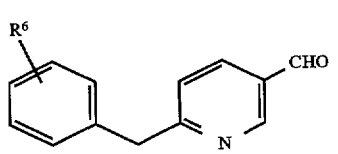
REACTION SCHEME AA
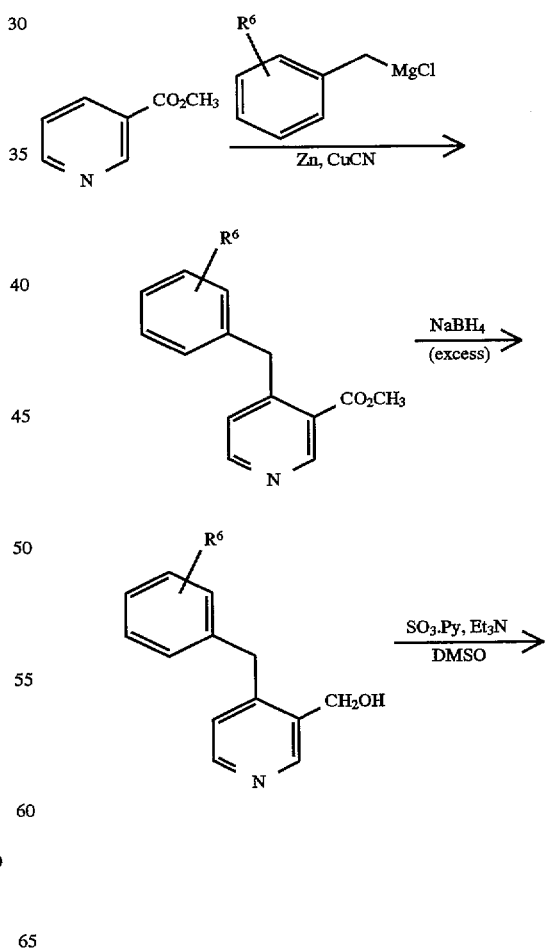

REACTION SCHEME AA -continued
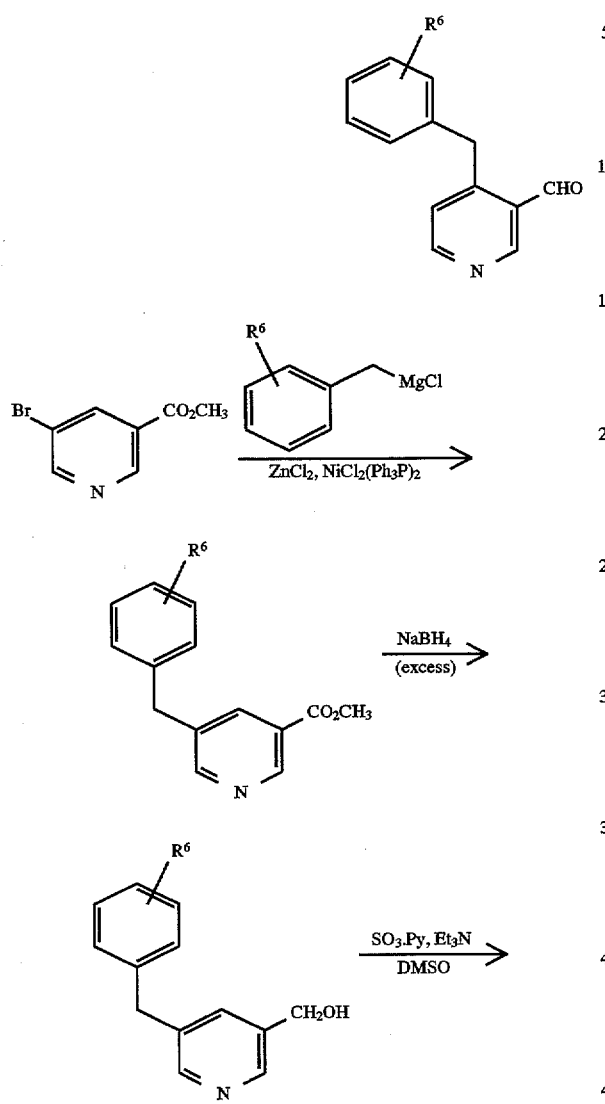
REACTION SCHEME BB -continued
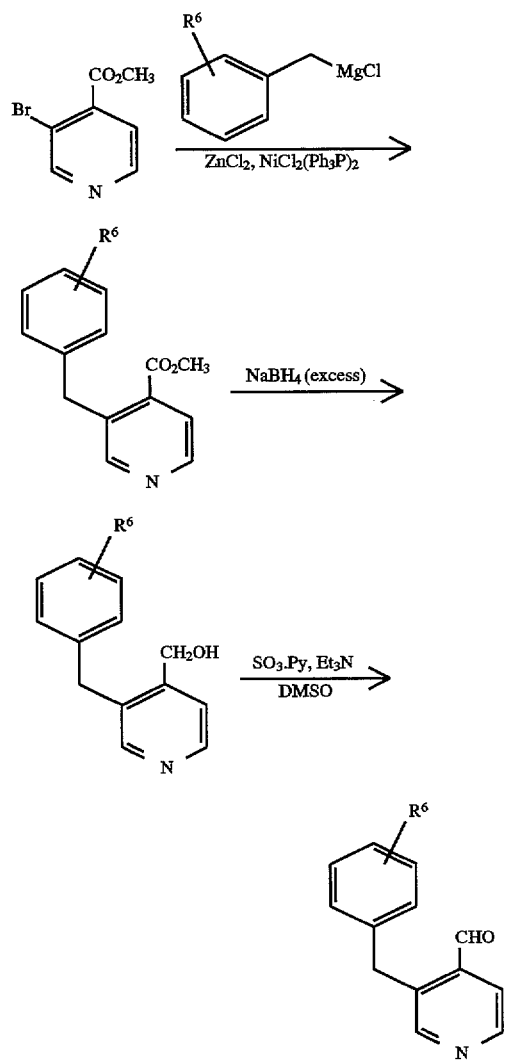
REACTION SCHEME CC
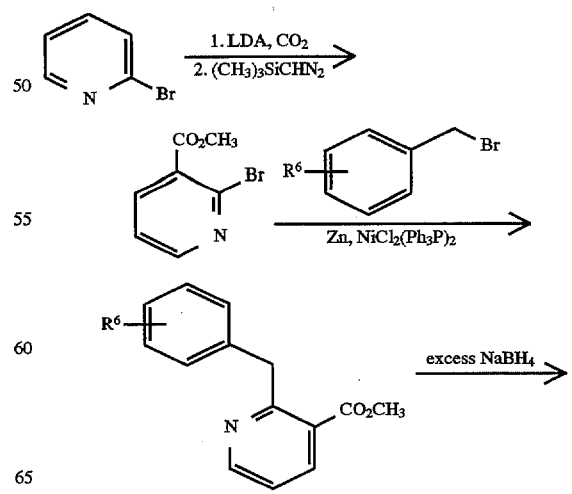
REACTION SCHEME BB
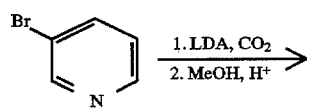

-continued
REACTION SCHEME CC

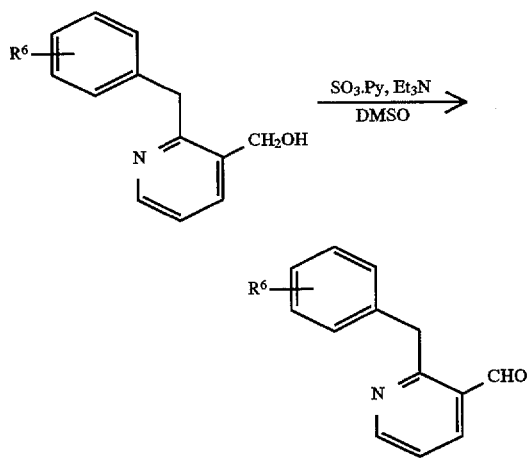

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, scr, abl, lck, fyn) or by other mechanisms.

The compounds of the instant invention inhibit farnesyl-protein transferase and the farnesylation of the oncogene protein Ras. The instant compounds may also inhibit tumor angiogenesis, thereby affecting the growth of tumors (J. Rak et al. *Cancer Research*, 55:4575–4580 (1995)). Such anti-angiogenesis properties of the instant compounds may also be useful in the treatment of certain forms of blindness related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of certain viral infections, in particular in the treatment of hepatitis delta and related viruses (J. S. Glenn et al. *Science*, 256:1331–1333 (1992).

The compounds of the instant invention are also useful in the prevention of restenosis after percutaneous transluminal coronary angioplasty by inhibiting neointimal formation (C. Indolfi et al. *Nature medicine*, 1:541–545(1995).

The instant compounds may also be useful in the treatment and prevention of polycystic kidney disease (D. L. Schaffner et al. *American Journal of Pathology*, 142:1051–1060 (1993) and B. Cowley, Jr. et al. *FASEB Journal*, 2:A3160 (1988)).

The instant compounds may also be useful for the treatment of fungal infections.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and tom starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 20 mg/kg of body weight per day, preferably of between 0.5 mg/kg of body weight to about 10 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

Example 1

N,N-bis(4-Imidazolemethyl)amino-3-[(3-carboxyphenyl)oxy]benzene hydrochloride (5)

Step 1: Preparation of 3-[(3-carbomethoxyphenyl)oxy] nitrobenzene (1)

A solution of methyl 3-iodobenzoate (2.54 g), 3-nitrophenol (1.48 g), and $K_2CO_3$ (3.97 g) in 60 mL of pyridine was warmed to 100° C. under nitrogen atmosphere. Copper powder (1.84 g) was added, and the reaction mixture was heated to reflux. After 22 h, The reaction was cooled to room temperature and poured into ethyl acetate and water. The organic layer was washed twice with 10% aq. HCl solution, then with sat. aq. $NaHCO_3$ solution, then with brine. The solution was dried ($Na_2SO_4$), filtered, and concentrated in vacuo to provide the crude product. Purification by silica gel chromatography ($CH_2Cl_2$) provided the product as a yellow oil.

Step 2: Preparation of 3-[(3-carbomethoxyphenyl)oxy]-aminobenzene (2)

To a solution of 1 (440 mg) in 30 mL of methanol under a nitrogen atmosphere was added 10% Pd/C (30 mg). The solution was purged with $H_2$ gas, then stirred at room temperature under a balloon atmosphere of $H_2$. After 8 h, the reaction was flushed with nitrogen and filtered through celite to remove the catalyst, then concentrated in vacuo. The resulting brown oil was used without further purification.

Step 3: Preparation of N,N-bis[(1-triphenylmethyl)-4-imidazolylmethyl)amino-3-[(3-carbomethoxyphenyl)oxy] benzene (3)

To a solution of 2 (312 mg) in 10 mL of 1,2-dichloroethane at 0° C. was added 4A powdered molecular sieves (650 mg) and sodium triacetoxyborohydride (1.32 g). 1-(Triphenylmethyl)-4-imidazole carboxaldehyde (1.17 g) was added, followed by 5 drops of acetic acid. The cooling bath was removed after 5 hours, and the reaction was stirred for another 15 hours. The reaction was poured into ethyl acetate and water. The organic layer was extracted with sat. aq. $NaHCO_3$ solution and brine, then dried ($Na_2SO_4$) and concentrated in vacuo to provide the product as a white solid.

Step 4: Preparation of N,N-bis[(1-triphenylmethyl)-4-imidazolylmethyl]amino-3-[(3-carboxyphenyl)oxy]benzene (4)

To a solution of 3 (400 mg) in 15 mL of 2:1:1 THF:methanol:$H_2O$ at room temperature was added solid NaOH (0.15 g). After 4 h, the reaction was cooled to 0° C. and acidified to pH~4 by dropwise addition of 10% aq. HCl solution. The solution was diluted with water and extracted three times with $CH_2Cl_2$. The combined organic layers were dried ($Na_2SO_4$) and concentrated in vacuo to provide the crude product.

Step 5: N,N-bis(4-Imidazolemethyl)amino-3-[(3-carboxyphenyl)oxy]benzene hydrochloride (5)

To a solution of 4 (380 mg) in 15 mL of $CH_2Cl_2$ was added triethylsilane (0.50 mL), followed by 5 mL of trifluoroacetic acid. The reaction was stirred for 30 minutes, then concentrated in vacuo, and partitioned with hexane and 2:1 water/MeOH. The water/MeOH solution was injected directly onto a Delta-Pak (C-18, 100A, 15 mm, 40 mm×100 mm) prep HPLC column. The gradient at 40 mL/min was 100% A (0.1% trifluoroacetic acid/water) for 5 min followed by 90% A to 45% A in 50 min (with B as 0.1% trifluoroacetic acid/acetonitrile). The pure fractions were pooled, concentrated in vacuo to near dryness, then taken up in 5 mL of water. This water solution was passed through a 2.0 g column of Bio-Rad AG 3-X4 chloride ion exchange resin with water rinses. The resulting aqueous column eluant was lyophilized 14 h to yield the title compound as a solid.

FAB mass spectrum m/e 390 (M+1).

Analysis calculated for $C_{20}H_{17}N_5O_3$.1.0 HCl.1.70 $H_2O$: C, 54.29; H, 4.88; N, 15.83; Found: C, 54.31; H, 4.85; N, 14.75.

Example 2

N,N-bis(4-Imidazolemethyl)amino-4-[(3-carboxyphenyl)oxy]benzene bis(trifluoroacetate)

Using the appropriate starring materials, the methods described above for Example 1 were used to prepare the title compound; except that, in step 5, ion exchange prior to lyophilization was omitted.

FAB mass spectrum m/e 390 (M+1).

Analysis calculated for $C_{20}H_{17}N_5O_3$.2.5 $CF_3CO_2H$.0.20 $H_2O$: C, 45.22; H, 3.02; N, 10.55; Found: C, 45.22; H, 3.18; N, 10.10.

Example 3

N,N-bis(4-Imidazolemethyl)amino-3-[(3-carbomethoxyphenyl)-oxy]benzene dihydrochloride Using the appropriate starring materials, the methods described above in Example 1 were employed to prepare the title compound, except that ester hydrolysis (Step 4) was omitted.

FAB mass spectrum m/e 404 (M+1).

Analysis calculated for $C_{22}H_{21}N_5O_3$.2.40 HCl.1.0 $H_2O$: C, 51.92; H, 5.03; N, 13.76; Found: C, 52.04; H, 5.03; N, 13.53.

Example 4

N,N-bis(4-Imidazolemethyl)amino-4-[(3-carbomethoxyphenyl)-oxy]benzene bis (trifluoroacetate)

Using the appropriate starring materials, the methods described above in Example 1 were employed to prepare the title compound, except that ester hydrolysis (Step 4) and ion exchange proir to lyophilization of the final product was omitted.

FAB mass spectrum m/e 404 (M+1).

Analysis calculated for $C_{22}H_{21}N_5O_3 \cdot 2.40\ CF_3CO_2H \cdot 0.20\ H_2O$: C, 47.29; H, 3.52; N, 10.29; Found: C, 47.26; H, 3.48; N, 10.25.

Example 5

N-(4-Imidazolemethyl)-N-(4-nitrobenzyl) aminomethyl-3-[(3-carboxyphenyl)oxy]benzene hydrochloride (9)

Step 1: Preparation of 3-[(3-carbomethoxyphenyl)oxy]benzaldehyde (6)

To a solution of NaH (washed with hexane, 564 mg) in 20 mL of pyridine at 0° C. was added methyl 3-hydroxybenzoate (1.95 g), and the solution was allowed to warm to room temperature. After 5 minutes, 3-bromobenzaldehyde (1.64 mL) was added, then $CuBr \cdot SMe_2$ (3.15 g). The solution was heated to reflux under a stream of nitrogen. After 24 h, the reaction was cooled to room temperature and poured into ethyl acetate and water. The organic layer was washed twice with 10% aq. HCl solution, then with sat. aq. $NaHCO_3$ solution, then with brine. The solution was dried ($Na_2SO_4$), filtered, and concentrated in vacuo to provide the crude product. Purification by silica gel chromatography ($CH_2Cl_2$) gave the titled compound as a yellow oil.

Step 2: Preparation of N-(4-nitrobenzyl)-N-[(1-triphenylmethyl)-4-imidazolylmethyl]aminomethyl-3-[(3-carbomethoxy-phenyl)oxy]benzene (7)

To a solution of 6 (245 mg) in 15 mL of 1,2-dichloroethane at 0° C. was added 4A powdered molecular sieves (550 mg) and sodium triacetoxyborohydride (320 mg). 4-Nitrobenzylamine hydrochloride was added, followed by 4 drops of AcOH. The cooling bath was removed, and the reaction was stirred for 13 hours. After returning the solution to 0° C., another portion of sodium triacetoxyborohydride (330 mg) was added, followed by 1-(triphenylmethyl)-4-imidazole carboxaldehyde (433 mg). The cooling bath was removed, and the reaction was stirred for another 4 hours. The reaction was poured into ethyl acetate and water. The organic layer was extracted with sat. aq. $NaHCO_3$ solution and brine, then dried ($Na_2SO_4$) and concentrated in vacuo to provide the crude product. Purification by silica gel chromatography (50–70% EtOAc/hexane) gave the titled compound as a white foam.

Step 3: Preparation of N-(4-nitrobenzyl)-N-[(1-triphenylmethyl)-4-imidazolylmethyl]aminomethyl-3-[(3-carboxyphenyl)oxy]-benzene (8)

The compound was prepared from 7 (78 mg) using the method described in Example 1 Step 4.

Step 4: N-(4-Imidazolemethyl)-N-(4-nitrobenzyl) aminomethyl-3-[(3-carboxyphenyl)oxy]benzene hydrochloride (9)

The compound was prepared from 8 (60 mg) using the method described in Example 1 Step 5.

FAB mass spectrum m/e 459 (M+1).

Analysis calculated for $C_{25}H_{22}N_4O_5 \cdot 0.90\ HCl \cdot 0.10\ H_2O$: C, 60.90; H, 4.72; N, 11.36; Found: C, 60.94; H, 4.71; N, 11.15.

Example 6

N-(4-Imidazolemethyl)-N-(4-nitrobenzyl) aminomethyl-3-[(3-carbomethoxyphenyl)oxy] benzene hydrochloride Using the appropriate starring materials, the methods described above in Example 5 were employed to prepare the title compound, except that ester hydrolysis (Step 4) was omitted.

FAB mass spectrum m/e 473 (M+1).

Analysis calculated for $C_{26}H_{24}N_4O_5 \cdot 0.10\ HCl \cdot 0.10\ H_2O$: C, 60.71; H, 4.96; N, 10.89; Found: C, 60.65; H, 4.80; N, 10.51.

Example 7

N-(4-Imidazolemethyl)-N-(4-nitrobenzyl)amino-3-(phenoxy)benzene hydrochloride (13)

Step 1: Preparation of 3-(phenoxy)nitrobenzene (10)

The compound above was prepared from 3-iodonitrobenzene (925 mg) and phenol, using the procedure described in Example 5 Step 1. The crude product was used without further purification.

Step 2: Preparation of 3-(phenoxy)aminobenzene (11)

To a solution of 10 (672 mg) in 20 mL of methanol was added iron powder (600 mg) and acetic acid (0.5 mL). The reaction was refluxed for 24 hours, then cooled to room temperature and poured into ethyl acetate and water. The organic layer was washed with water, sat. aq. $NaHCO_3$ solution, and brine. The solution was dried ($Na_2SO_4$), filtered, and concentrated in vacuo to provide the crude product.

Step 3: Preparation of N-(4-nitrobenzyl)-N-[(1-triphenylmethyl)-4-imidazolylmethyl]amino-3-(phenoxy)benzene (12)

To a solution of 11 (210 mg) in 15 mL of 1,2-dichloroethane at 0° C. was added 4A powdered molecular sieves (480 mg) and sodium triacetoxyborohydride (365 mg). 4-Nitrobenzaldehyde was added (183 mg), followed by 4 drops of AcOH. The cooling bath was removed, and the reaction was stirred for 3 hours. After returning the solution to 0° C., another portion of sodium triacetoxyborohydride (360 mg) was added, followed by 1-(triphenylmethyl)-4-imidazole carboxaldehyde (570 mg). The cooling bath was removed, and the reaction was stirred for another 15 hours. The reaction was poured into ethyl acetate and water. The organic layer was extracted with sat. aq. $NaHCO_3$ solution and brine, then dried ($Na_2SO_4$) and concentrated in vacuo to provide the crude product. Purification by silica gel chromatography (1% $MeOH/CH_2Cl_2$) gave the titled compound as an orange foam.

Step 4: N-(4-Imidazolemethyl)-N-(4-nitrobenzyl)amino-3-(phenoxy)benzene hydrochloride (13)

The titled compound was prepared from 12 using the method in Step 5 of Example 1.

FAB mass spectrum m/e 401 (M+1).

Analysis calculated for $C_{23}H_{20}N_4O_3 \cdot 0.80\ HCl \cdot 0.20\ H_2O$ C, 63.77; H, 4.93; N, 12.93; Found: C, 63.82; H, 4.92; N, 12.80.

Example 8

N-(4-Imidazolemethyl)-N-(4-nitrobenzyl)amino-4-(phenoxy)benzene hydrochloride (17)

Step 1: Preparation of 4-(phenoxy)nitrobenzene (14)

To a solution of 4-fluoronitrobenzene (0.50 mL) and phenol (443 mg) in 5.0 mL of dimethylformamide was added $K_2CO_3$ (1.27 g). The reaction was warmed to 70° C. for 20 h, then cooled to room temperature and poured into ethyl acetate and water. The organic layer was washed with water, sat. aq. $NaHCO_3$ solution, and brine. The solution was dried ($Na_2SO_4$), filtered, and concentrated in vacuo to provide the crude product as a yellow solid.

Step 2: Preparation of 4-(phenoxy)aminobenzene (15)

The titled compound was prepared from 14 (957 mg) using the method in Step 2 of Example 7.

45

Step 3: Preparation of N-(4-nitrobenzyl)-N-[(1-triphenylmethyl)-4-imidazolylmethyl]amino-4-(phenoxy)benzene (16)

The titled compound was prepared from 15 (197 mg) using the method in Step 3 of Example 7.

Step 4: N-(4-Imidazolemethyl)-N-(4-nitrobenzyl)amino-4-(phenoxy)benzene hydrochloride (17)

The titled compound was prepared from 16 using the method in Step 5 of Example 1.

FAB mass spectrum m/e 401 (M+1).

Analysis calculated for $C_{23}H_{20}N_4O_3 \cdot 0.70$ HCl$\cdot 0.30$ H$_2$O C, 64.04; H, 4.98; N, 12.99; Found: C, 64.16; H, 4.94; N, 12.86.

Example 9

N-(4-Imidazolemethyl)-N-(4-nitrobenzyl)amino-4-(phenylthio)benzene triflouroacetate Using the appropriate starting materials, the methods described above for Example 8 were used to prepare the title compound, except that ion exchange prior to lyophilization of the final product was omitted.

FAB mass spectrum m/e 417 (M+1).

Analysis calculated for $C_{23}H_{20}N_4O_2S \cdot 1.60$ CF$_3$CO$_2$H: C, 52.38; H, 3.66; N, 9.33; Found: C, 52.37; H, 3.67; N, 9.97.

Example 10

N-Butyl-N-[1-(4-cyanobenzyl)-5-imidazolemethyl]amino-4-(phenoxy)benzene hydrochloride (20)

Step 1: Preparation of N-[(1-triphenylmethyl)-4-imidazolylmethyl]amino-4-(phenoxy)benzene (18)

To a solution of 15 (443 mg) in 15 mL of 1,2-dichloroethane at 0° C. was added 4A powdered molecular sieves (1.10 g) and sodium triacetoxyborohydride (740 mg). 1-(Triphenylmethyl)-4-imidazole carboxaldehyde (787 mg) and acetic acid (4 drops) were added, the cooling bath was removed, and the reaction was stirred for 15 hours. The reaction was poured into ethyl acetate and water. The organic layer was extracted with sat. aq. NaHCO$_3$ solution and brine, then dried (Na$_2$SO$_4$) and concentrated in vacuo to provide the crude product.

Step 2: Preparation of N-butyl-N-[(1-triphenylmethyl)-4-imidazolylmethyl]amino-4-(phenoxy)benzene (19)

The compound above was prepared from 18 (593 mg) using the procedure described above for the preparation of 18, except that n-butyraldehyde was used in place of 1-(triphenylmethyl)-4-imidazole carboxaldehyde. The crude product was used without further purification.

Step 3: N-Butyl-N'-[1-(4-cyanobenzyl)-5-imidazolemethyl]amino-4-(phenoxy)benzene hydrochloride (20)

To a solution of 19 (278 mg) in 4.0 mL of acetonitrile at room temperature was added p-cyanobenzyl bromide (108 mg). After 13 h, the solution was concentrated in vacuo to provide a pale yellow foam. This was taken up in 10 mL of CH$_2$Cl$_2$, and triethylsilane (0.25 mL) was added followed by 5 mL of trifluoroacetic acid. The reaction was stirred for 1 hour, then concentrated in vacuo, and partitioned with hexane and 2:1 water/MeOH. The water/MeOH solution was injected directly onto a Delta-Pak (C-18, 100A, 15 mm, 40 mm×100 mm) prep HPLC column. The gradient at 40 mL/min was 100% A (0.1% trifluoroacetic acid/water) for 5 min followed by 90% A to 45% A in 50 min (with B as 0.1% trifluoroacetic acid/acetonitrile). The pure fractions were pooled, concentrated in vacuo to near dryness, then taken up in 5 mL of water and 1 mL of acetonitrile. This solution was

46 passed through a 2.0 g column of Bio-Rad AG 3-X4 chloride ion exchange resin with water rinses. The resulting aqueous column eluant was lyophilized 14 h to yield the title compound as a solid.

FAB mass spectrum m/e 437 (M+1).

Analysis calculated for $C_{28}H_{28}N_4O \cdot 1.0$ HCl: C, 71.10; H, 6.18; N, 11.84; Found: C, 71.68; H, 6.28; N, 11.78.

Example 11

N-[1-(4-Cyanobenzyl)-5-imidazolemethyl]amino-4-(phenoxy)benzene trifluoroacetate The title compound was prepared from 18 (243 mg) using the procedure described above in Example 10 Step 3, except that ion exchange prior to lyophilization was omitted.

FAB mass spectrum m/e 381 (M+1).

Analysis calculated for $C_{24}H_{20}N_4O \cdot 1.60$ CF$_3$CO$_2$H$\cdot 0.50$ H$_2$O: C, 57.13; H, 3.98; N, 9.80; Found: C, 57.19; H, 3.88; N, 9.93.

Example 12

N-(4-Imidazolemethyl)amino-3-[(3-carboxyphenyl)oxy]benzene trifluoroacetate

Using compound 2 as the starting material, the methods described in Example 10, Step 1 and Example 1, Steps 4 and 5 were used to prepare the title compound, except that ion exchange prior to lyophilization of the final product was omitted.

FAB mass spectrum m/e 310 (M+1).

Analysis calculated for $C_{17}H_{15}N_3O_3 \cdot 1.70$ CF$_3$CO$_2$H$\cdot 0.30$ H$_2$O: C, 48.18; H, 3.43; N, 8.26; Found: C, 48.13; H, 3.35; N, 8.54.

Example 13

1-[N-(1-(4-cyanobenzyl)-5-imidazolylmethyl)-N-(4-cyanobenzyl)amino]-4-(phenoxy)benzene hydrochloride The titled compound was prepared from 18 using the procedure described in Steps 2 and 3 of Example 10, except that in Step 2, p-cyanobenzaldehyde was used in place of n-butyraldehyde.

FAB mass spectrum m/e 496 (M+1).

Analysis calculated for $C_{32}H_{25}N_5O \cdot 1.40$ HCl: C, 70.31; H, 4.87; N, 12.81; Found: C, 70.29; H, 4.84; N, 12.06.

Example 14

(±)-4-[(4-imidazolylmethyl)amino]pentyl-1-(phenoxy)benzene trifluoroacetate

Step 1: Preparation of (±)-4-[(hydroxy)pentyl]-1-(phenoxy)benzene

To a solution of 4-phenoxybenzaldehyde (704 mg, 3.56 mmol) in 15 mL of THF at −78° C. was added n-BuLi dropwise (3.73 mmol, 2.5M in hexane). After 24 hours, the reaction was poured into ethyl acetate and sat. aq. NaHCO$_3$ solution, then washed with brine, dried (Na$_2$SO$_4$) and concentrated in vacuo to provide the crude product.

Step 2: Preparation of (±)-4-[(azido)pentyl]-1-(phenoxy)benzene

To a solution of the product from Step 1 (3.5 mmol) in 15 mL of THF at −0° C. was added triphenylphosphine (921 mg), followed by diethylazodicarboxylate (0.55 mL) and diphenylphosphoryl azide (0.75 mL). The solution was allowed to warm to room temperature overnight. After 48 hours, the reaction was poured into ethyl acetate and sat. aq. NaHCO$_3$ solution, then washed with brine, dried (Na$_2$SO$_4$) and concentrated in vacuo to provide the crude product. Purification by chromatography on silica gel (50% CH$_2$Cl$_2$/hexane) provided 360 mg of the titled compound.

Step 3: Preparation of (±)-4-[(amino)pentyl]-1-(phenoxy) benzene

To a solution of the product from Step 2 (360 mg, 1.28 mmol) in 10 mL of THF at room temperature was added water (0.025 mL), followed by triphenylphosphine (364 mg, 1.41 mmol). The solution was stirred at room temperature. After 84 hours, the reaction was concentrated in vacuo to provide the titled compound.

Step 4: Preparation of (±)-4-[(4-imidazolylmethyl)amino] pentyl-1-(phenoxy)benzene trifluoroacetate The compound above was prepared from the product of Step 3 using the procedures described in Steps 3 and 5 of Example 1, except that in Step 5, ion exchange prior to lyophilization was omitted.

FAB mass spectrum m/e 336 (M+1).

Analysis calculated for C$_{21}$H$_{25}$N$_3$O.2.60 CF$_3$CO$_2$H.0.80 H$_2$O: C, 48.69; H, 4.55; N, 6.50; Found: C, 48.65; H, 4.48; N, 6.60.

Example 15

1-[(N-(1-(4-cyanobenzyl)-5-imidazolylmethyl)-N-(n-butyl)amino)methyl]-4-(phenoxy)benzene hydrochloride The titled compound was prepared from 4-phenoxybenzaldehyde using the procedure described in Example 5 Step 2 (except that n-propylamine was used in place of 4-nitrobenzylamine) followed by the procedure described in Example 10, Step 3.

FAB mass spectrum m/e 451 (M+1).

Analysis calculated for C$_{29}$H$_{30}$N$_4$O.1.30 HCl: C, 69.95; H, 6.34; N, 11.25; Found: C, 69.89; H, 6.33; N, 11.39.

Example 16

4-[N-(1-(4-cyanobenzyl)-5-imidazolylmethyl)-N-(n-butyl)amino]-1-(phenylthio)benzene hydrochloride Step 1: Preparation of 4-(phenylthio)aniline The titled compound was prepared from 4-fluoronitrobenzene and thiophenol using the procedures in Steps 1 and 2 of Example 8.

Step 2: Preparation of N-butyl-N-[(1-triphenylmethyl)-4-imidazolylmethyl]amino-4-(phenylthio)benzene The titled compound was prepared from the product of Step 1 using the procedures described in Steps 1 and 2 of Example 10.

Step 3: Preparation of 4-[N-(1-(4-cyanobenzyl)-5-imidazolylmethyl)-N-(n-butyl)amino]-1-(phenylthio) benzene hydrochloride The titled compound was prepared from the product of Step 2 using the procedure described in Step 3 of Example 10.

FAB mass spectrum m/e 453 (M+1).

Analysis calculated for C$_{28}$H$_{28}$N$_4$S.2.70 HCl.0.50 H$_2$O: C, 60.05; H, 5.71; N, 10.00; Found: C, 60.12; H, 5.72; N, 9.55.

Example 17

(±)-4-[N-(1-(4-cyanobenzyl)-4-imidazolylmethyl)-N-(n-butyl)amino]-1-(phenylsulfinyl)benzene hydrochloride Step 1: Preparation of (±)-4-[N-(4-imidazolylmethyl)-N-(n-butyl)amino]-1-(phenylsulfinyl)benzene To a solution of the sulfide product from Step 2 of Example 16 (614 mg, 1.06 mmol) in 20 mL of 25% aqueous acetone at room temperature was added sodium metaperiodate (1.80 g). After 72 hours, the reaction was poured into ethyl acetate and sat. aq. NaHCO$_3$ solution, then washed with brine, dried (Na$_2$SO$_4$) and concentrated in vacuo to provide the crude product. Purification by chromatography on silica gel (2–5% MeOH/CH$_2$Cl$_2$) provided 172 mg of the titled compound.

Step 2: Preparation of (±)-4-[N-(1-(4-cyanobenzyl)-4-imidazolylmethyl)-N-(n-butyl)amino]-1-(phenylsulfinyl) benzene hydrochloride To a solution of the product from Step 1 (172 mg, 0.466 mmol) in 5 mL of DMF at 0° C. was added sodium hydride (37 mg, 60% dispersion in mineral oil), followed by p-cyanobenzylbromide (109 mg, 0.508 mmol). After 1 hour, the reaction was poured into ethyl acetate and sat. aq. NaHCO$_3$ solution, then washed with brine, dried (Na$_2$SO$_4$) and concentrated in vacuo to provide the crude product. The product was taken up in water/MeOH solution and was injected directly onto a Delta-Pak (C-18, 100A, 15 mm, 40 mm×100 mm) prep HPLC column. The gradient at 40 mL/min was 100% A (0.1% trifluoroacetic acid/water) for 5 min followed by 90% A to 45% A in 50 min (with B as 0.1% trifluoroacetic acid/acetonitrile). The pure fractions were pooled, concentrated in vacuo to near dryness, then taken up in 5 mL of water and 1 mL of acetonitrile. This solution was passed through a 2.0 g column of Bio-Rad AG 3-X4 chloride ion exchange resin with water rinses. The resulting aqueous column eluant was lyophilized 14 h to yield the title compound as a solid.

FAB mass spectrum m/e 469 (M+1).

Analysis calculated for C$_{28}$H$_{28}$N$_4$OS.1.80 HCl.0.30 H$_2$O: C, 66.83; H, 5.89; N, 11.13; Found: C, 66.72; H, 5.91; N, 11.17.

Example 18

3-[N-(4-imidazolylmethyl)-N-(n-butyl)amino]-N-(phenyl)benzenesulfonamide hydrochloride Step 1: Preparation of 3-nitro-1-N-(phenyl) benzenesulfonamide To a solution of 3-nitrobenzenesulfonyl chloride (3.08 g, 13.9 mmol) in 28 mL of dichloromethane was added triethylamine (3.88 mL, 27.8 mmol) and aniline (1.39 mL. 15.3 mmol). After 16 hours, the reaction was poured into ethyl acetate and 10% HCl solution, then washed with brine, dried (MgSO$_4$) and concentrated in vacuo to provide the crude product. Purification by chromatography on silica gel (25–50% CH$_2$Cl$_2$/hexane, then 5% MeOH/CH$_2$Cl$_2$) provided 1.68 g of the desired product as an off-white solid.

Step 2: Preparation of 3-amino-1-N-(phenyl) benzenesulfonamide

The titled compound was prepared from the product of Step 1 using the procedure described in Step 2 of Example 7.

Step 3: Preparation of 3-[N-butyl-N-((1-triphenylmethyl)-4-imidazolylmethyl)amino]-1-N-(phenyl) benzenesulfonamide The titled compound was prepared from the product of Step 2 using the procedures described in Steps 1 and 2 of Example 10. In Step 2, benzene was used as a solvent instead of 1,2-dichloroethane.

Step 4: Preparation of 3-[N-(4-imidazolylmethyl)-N-(n-butyl)amino]-N-(phenyl)benzenesulfonamide hydrochloride The titled compound was prepared from the product of Step 3 using the procedure described in Step 5 of Example 1.

FAB mass spectrum m/e 385 (M+1).

Analysis calculated for $C_{20}H_{24}N_4O_2S \cdot 1.50$ HCl: C, 54.73; H, 5.86; N, 12.76; Found: C, 54.74; H, 5.70; N, 12.69.

Example 19

1-[N-(1-(4-cyanobenzyl)-5-imidazolylmethyl)amino]-3-methoxy-4-phenylbenzene

Step 1: Preparation of 1-triphenylmethyl-4-(hydroxymethyl)-imidazole

To a solution of 4-(hydroxymethyl)imidazole hydrochloride (35 g) in 250 mL of dry DMF at room temperature was added triethylamine (90.6 mL). A white solid precipitated from the solution. Chlorotriphenylmethane (76.1 g) in 500 mL of DMF was added dropwise. The reaction mixture was stirred for 20 hours, poured over ice, filtered, and washed with ice water. The resulting product was slurried with cold dioxane, filtered, and dried in vacuo to provide the titled product as a white solid which was sufficiently pure for use in the next step.

Step 2: Preparation of 1-triphenylmethyl-4-(acetoxymethyl)-imidazole

The product from Step 1 was suspended in 500 mL of pyridine. Acetic anhydride (74 mL) was added dropwise, and the reaction was stirred for 48 hours during which it became homogeneous. The solution was poured into 2 L of EtOAc, washed with water (3×1 L), 5% aq. HCl soln. (2×1 L), sat. aq. NaHCO$_3$, and brine, then dried (Na$_2$SO$_4$), filtered, and concentrated in vacuo to provide the crude product. The titled acetate product was isolated as a white powder (85.8 g) which was sufficiently pure for use in the next step.

Step 3: Preparation of 1-(4-cyanobenzyl)-5-(acetoxymethyl) imidazole hydrobromide A solution of the product from Step 2 (85.8 g) and α-bromo-p-tolunitrile (50.1 g) in 500 mL of EtOAc was stirred at 60° C. for 20 hours, during which a pale yellow precipitate formed. The reaction was cooled to room temperature and filtered to provide the solid imidazolium bromide salt. The filtrate was concentrated in vacuo to a volume 200 mL, reheated at 60° C. for two hours, cooled to room temperature, and filtered again. The filtrate was concentrated in vacuo to a volume 100 mL, reheated at 60° C. for another two hours, cooled to room temperature, and concentrated in vacuo to provide a pale yellow solid. All of the solid material was combined, dissolved in 500 mL of methanol, and warmed to 60° C. After two hours, the solution was reconcentrated in vacuo to provide a white solid which was triturated with hexane to remove soluble materials. Removal of residual solvents in vacuo provided the titled product hydrobromide as a white solid (50.4 g, 89% purity by HPLC) which was used in the next step without further purification.

Step 4: Preparation of 1-(4-cyanobenzyl)-5-(hydroxymethyl)-imidazole

To a solution of the acetate from Step 3 (50.4 g) in 1.5 L of 3:1 THF/water at 0° C. was added lithium hydroxide monohydrate (18.9 g). After one hour, the reaction was concentrated in vacuo, diluted with EtOAc (3 L), and washed with water, sat. aq. NaHCO$_3$ and brine. The solution was then dried (Na$_2$SO$_4$), filtered, and concentrated in vacuo to provide the crude product (26.2 g) as a pale yellow fluffy solid which was sufficiently pure for use in the next step without further purification.

Step 5: Preparation of 1-(4-cyanobenzyl)-5-imidazolecarboxaldehyde

To a solution of the alcohol from Step 4 (21.5 g) in 500 mL of DMSO at room temperature was added triethylamine (56 mL), then SO$_3$-pyridine complex (40.5 g). After 45 minutes, the reaction was poured into 2.5 L of EtOAc, washed with water (4×1 L) and brine, dried (Na$_2$SO$_4$), filtered, and concentrated in vacuo to provide the titled aldehyde (18.7 g) as a white powder which was sufficiently pure for use in the next step without further purification.

Step 6: Preparation of 1-[N-(1-(4-cyanobenzyl)-5-imidazolylmethyl)amino]-3-methoxy-4-phenylbenzene The titled compound was prepared from the product of Step 5 and 1-amino-3-methoxy-4-phenylbenzene using the procedure described in Step 3 of Example 1.

Analysis calculated for $C_{25}H_{22}N_4O$: C, 73,38; H, 6.07; N, 12.53; Found: C, 73.36; H, 6.00; N, 12.49.

Example 20

In vitro inhibition of ras farnesyl transferase

Assays of farnesyl-protein transferase. Partially purified bovine FPTase and Ras peptides (Ras-CVLS, Ras-CVIM and RAS-CAIL) were prepared as described by Schaber et al., *J. Biol. Chem.* 265:14701–14704 (1990), Pompliano, et al., *Biochemistry* 31:3800 (1992) and Gibbs et al., *PNAS U.S.A.* 86:6630–6634 (1989), respectively. Bovine FPTase was assayed in a volume of 100 μl containing 100 mM N-(2-hydroxy ethyl) piperazine-N'-(2-ethane sulfonic acid) (HEPES), pH 7.4, 5 mM MgCl$_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 μg/ml FPTase at 31° C. for 60 min. Reactions were initiated with FPTase and stopped with 1 ml of 1.0M HCL in ethanol. Precipitates were collected onto filter-mats using a TomTec Mach II cell harvestor, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 μM ZnCl$_2$ and 100 nM Ras-CVIM were added to the reaction mixture. Reactions were performed for 30 min., stopped with 100 μl of 30% (v/v) trichloroacetic acid (TCA) in ethanol and processed as described above for the bovine enzyme.

The compounds of the instant invention were tested for inhibitory activity against human FPTase by the assay described above and were found to have IC$_{50}$ of <100 μM.

Example 21

In vivo ras farnesylation assay

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13–259 (Furth, M. E. et al., J. Virol. 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 22

In vivo growth inhibition assay

To determine the biological consequences of FPTase inhibition, the effect of the compounds of the instant invention on the anchorage-independent growth of Rat 1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of $1 \times 10^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0.1% methanol or the concentration of the instant compound. Photomicrographs are taken 16 days after the cultures are seeded and comparisons are made.

What is claimed is:

1. A compound which inhibits farnesyl-protein transferase having the Formula I:

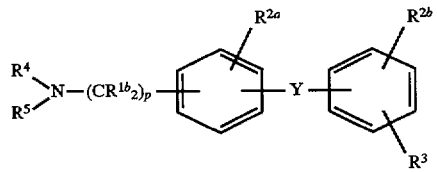

wherein:

$R^{1a}$ and $R^{1b}$ are independently selected from:
 a) hydrogen,
 b) unsubstituted or substituted aryl, unsubstituted or substituted heterocycle, unsubstituted or substituted $C_3-C_6$ cycloalkyl, $C_2-C_6$ alkenyl, $C_2-C_6$ alkynyl, $R^8O-$, $R^9S(O)_m-$, $R^8C(O)NR^8-$, CN, $NO_2$, $(R^8)_2N-C(NR^8)-$, $R^8C(O)-$, $R^8OC(O)-$, $N_3$, $-N(R^8)_2$, or $R^9OC(O)NR^8-$,
 c) $C_1-C_6$ alkyl unsubstituted or substituted by unsubstituted or substituted aryl, unsubstituted or substituted heterocyclic, unsubstituted or substituted $C_3-C_6$ cycloalkyl, $C_2-C_6$ alkenyl, $C_2-C_6$ alkynyl, $R^8O-$, $R^9S(O)_m-$, $R^8C(O)NR^8-$, CN, $(R^8)_2N-$ $C(NR^8)-$, $R^8C(O)-$, $R^8OC(O)-$, $N_3$, $-N(R^8)_2$, or $R^9OC(O)-NR^8-$;

$R^{2a}$, $R^{2b}$ and $R^3$ are independently selected from:
 a) hydrogen,
 b) $C_1-C_6$ alkyl unsubstituted or substituted by $C_2-C_6$ alkenyl, $R^8O-$, $R^9S(O)_m-$, $R^8C(O)NR^8-$, CN, $N_3$, $(R^8)_2N-C(NR^8)-$, $R^8C(O)-$, $R^8OC(O)-$, $-N(R^8)_2$, or $R^9OC(O)NR^8-$,
 c) unsubstituted or substituted aryl, unsubstituted or substituted heterocycle, unsubstituted or substituted cycloalkyl, alkenyl, $R^8O-$, $R^9S(O)_m-$, $R^8C(O)NR^8-$, CN, $NO_2$, $(R^8)_2N-C(NR^8)-$, $R^8C(O)-$, $R^8OC(O)-$, $N_3$, $-N(R^8)_2$, halogen or $R^9OC(O)NR^8-$, and
 d) $C_1-C_6$ alkyl substituted with an unsubstituted or substituted group selected from aryl, heterocyclic and $C_3-C_{10}$ cycloalkyl; provided that heterocycle is not tetrazolyl;

$R^4$ and $R^5$ are independently selected from:
 a) hydrogen, and

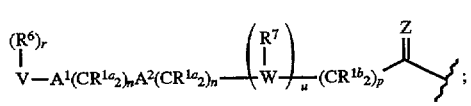

$R^6$ is independently selected from:
 a) hydrogen,
 b) unsubstituted or substituted aryl, unsubstituted or substituted heterocycle, unsubstituted or substituted $C_3-C_6$ cycloalkyl, $C_2-C_6$ alkenyl, $C_2-C_6$ alkynyl, $C_1-C_6$ perfluoroalkyl, F, Cl, Br, $R^8O-$, $R^9S(O)_m-$, $R^8C(O)NR^8-$, CN, $NO_2$, $R^8_2N-C(NR^8)-$, $R^8C(O)-$, $R^8OC(O)-$, $N_3$, $-N(R^8)_2$, or $R^9OC(O)NR^8-$, and
 c) $C_1-C_6$ alkyl unsubstituted or substituted by unsubstituted or substituted aryl, unsubstituted or substituted heterocycle, unsubstituted or substituted $C_3-C_6$ cycloalkyl, $C_2-C_6$ alkenyl, $C_2-C_6$ alkynyl, $C_1-C_6$ perfluoroalkyl, F, Cl, Br, $R^8O-$, $R^9S(O)_m-$, $R^8C(O)NH-$, CN, $H_2N-C(NH)-$, $R^8C(O)-$, $R^8OC(O)-$, $N_3$, $-N(R^8)_2$, or $R^8OC(O)NH-$;

$R^7$ is selected from:
 a) hydrogen,
 b) $C_2-C_6$ alkenyl, $C_2-C_6$ alkynyl, $C_1-C_6$ perfluoroalkyl, F, Cl, Br, $R^8O-$, $R^9S(O)_m-$, $R^8C(O)NR^8-$, CN, $NO_2$, $(R^8)_2N-C-(NR^8)-$, $R^8C(O)-$, $R^8OC(O)-$, $N_3$, $-N(R^8)_2$, or $R^9OC(O)NR^8-$, and
 c) $C_1-C_6$ alkyl unsubstituted or substituted by $C_1-C_6$ perfluoroalkyl, F, Cl, Br, $R^8O-$, $R^9S(O)_m-$, $R^8C(O)NR^8-$, CN, $(R^8)_2N-C(NR^8)-$, $R^8C(O)-$, $R^8OC(O)-$, $N_3$, $-N(R^8)_2$, or $R^9OC(O)NR^8-$;

$R^8$ is independently selected from hydrogen, $C_1-C_6$ alkyl, substituted or unsubstituted $C_1-C_6$ aralkyl and substituted or unsubstituted aryl;

$R^9$ is independently selected from $C_1-C_6$ alkyl and aryl;

$R^{10}$ is independently selected from hydrogen, $C_1-C_6$ alkyl, substituted or unsubstituted $C_1-C_6$ aralkyl and substituted or unsubstituted aryl;

$A^1$ and $A^2$ are independently selected from: a bond, $-CH=CH-$, $-C\equiv C-$, $-C(O)-$, $-C(O)NR^8-$, $-NR^8C(O)-$, O, $-N(R^8)-$, $-S(O)_2N(R^8)-$, $-N(R^8)S(O)_2-$, or $S(O)_m$;

V is selected from:
 a) hydrogen,

53 b) heterocycle,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle, provided that if W is imidazolyl, the point of attachment of the imidazolyl moiety to $(CR_2^{1b})_p$ is selected from the group consisting of 4 or 5 position carbon of the imidazolyl moiety;

Y is selected from: a bond, —C($R^{10}$)=C($R^{10}$)—, —C≡C—, —C(O)—, —C($R^{10}$)$_2$—, —C(O$R^{10}$)$R^{10}$—, —CN($R^{10}$)$_2R^{10}$—, —OC($R^{10}$)$_2$—, —N$R^{10}$C($R^{10}$)$_2$—, —C($R^{10}$)$_2$O—, —C($R^{10}$)$_2$N$R^{10}$—, —C(O)N$R^{10}$—, —N$R^{10}$C(O), O, —NC(O)$R^{10}$—, —NC(O)O$R^{10}$—, —S(O)$_2$N($R^{10}$)—, —N($R^{10}$)S(O)$_2$—, or S(O)$_m$;

Z is $H_2$ or O;
m is 0, 1 or 2;
n is 0, 1, 2, 3 or 4;
p is 0, 1, 2, 3 or 4;
r is 0 to 5, provided that r is 0 when V is hydrogen; and
u is 0 or 1;
or a pharmaceutically acceptable salt thereof.

2. A compound which inhibits Ras farnesyl-transferase having the Formula Ia:

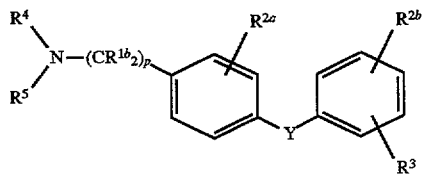

wherein:

$R^{1a}$ is independently selected from: hydrogen or $C_1$–$C_6$ alkyl;

$R^{1b}$ is independently selected from:
a) hydrogen,
b) unsubstituted or substituted aryl, unsubstituted or substituted heterocycle, unsubstituted or substituted $C_3$–$C_6$ cycloalkyl, $R^8O$—, —N($R^8$)$_2$ or $C_2$–$C_6$ alkenyl,
c) $C_1$–$C_6$ alkyl unsubstituted or substituted with 1 or 2 substituents selected from: unsubstituted or substituted aryl, unsubstituted or substituted heterocycle, unsubstituted or substituted $C_3$–$C_6$ cycloalkyl, $C_2$–$C_6$ alkenyl, $R^8O$—, and —N($R^8$)$_2$;

$R^{2a}$ and $R^{2b}$ are independently selected from:
a) hydrogen,
b) $C_1$–$C_6$ alkyl unsubstituted or substituted by a substituent selected from: $R^8O$—, —N($R^8$)$_2$, and $R^9S(O)_m$—,
c) substituted or unsubstituted aryl, and
d) halogen selected from F, I, Cl and Br;

$R^3$ is selected from:
a) hydrogen,
b) $C_1$–$C_6$ alkyl unsubstituted or substituted by a substituent selected from: $R^8O$—, —N($R^8$)$_2$ and $R^9S(O)_m$—,
c) substituted or unsubstituted aryl,
d) halogen selected from F, I, Cl and Br, and
e) —CO$_2R^8$;

54

$R^4$ and $R^5$ are independently selected from:
a) hydrogen, and b) 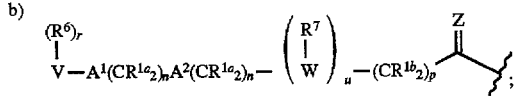

$R^6$ is selected from:
a) hydrogen,
b) substituted or unsubstituted aryl, $C_1$–$C_6$ alkyl, $C_2$–$C_6$ alkenyl, $C_2$–$C_6$ alkynyl, $C_1$–$C_6$ perfluoroalkyl, F, Cl, $R^8O$—, $R^8C(O)NR^8$—, CN, NO$_2$, ($R^8$)$_2$N—C(N$R^8$)—, $R^8C(O)$—, $R^8OC(O)$—, —N($R^8$)$_2$, or $R^9OC(O)NR^8$—, and
c) $C_1$–$C_6$ alkyl substituted by $C_1$–$C_6$ perfluoroalkyl, $R^8O$—, $R^8C(O)NR^8$—, ($R^8$)$_2$N—C(N$R^8$)—, $R^8C(O)$—, $R^8OC(O)$—, —N($R^8$)$_2$, or $R^9OC(O)NR^8$—;

$R^7$ is selected from:
a) hydrogen,
b) $C_2$–$C_6$ alkenyl, $C_2$–$C_6$ alkynyl, $C_1$–$C_6$ perfluoroalkyl, F, Cl, $R^8O$—, $R^9S(O)_m$—, $R^8C(O)NR^8$—, CN, NO$_2$, ($R^8$)$_2$N—C(N$R^8$)—, $R^8C(O)$—, $R^8OC(O)$—, —N($R^8$)$_2$, or $R^9OC(O)NR^8$—, and
c) $C_1$–$C_6$ alkyl unsubstituted or substituted by $C_1$–$C_6$ perfluoroalkyl, F, Cl, $R^8O$—, $R^9S(O)_m$—, $R^8C(O)NR^8$—, CN, ($R^8$)$_2$N—C(N$R^8$)—, $R^8C(O)$—, $R^8OC(O)$—, —N($R^8$)$_2$, or $R^9OC(O)NR^8$—;

$R^8$ is independently selected from hydrogen, $C_1$–$C_6$ alkyl, substituted or unsubstituted $C_1$–$C_6$ aralkyl and substituted or unsubstituted aryl;

$R^9$ is independently selected from $C_1$–$C_6$ alkyl and aryl;

$R^{10}$ is independently selected from hydrogen, $C_1$–$C_3$ alkyl and benzyl;

$A^1$ and $A^2$ are independently selected from: a bond, —CH=CH—, —C≡C—, —C(O)—, —C(O)N$R^8$—, O, —N($R^8$)—, or S(O)$_m$;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

W is a heterocycle selected from pyrrolidinyl, imidazolyl, imidazolinyl, pyridinyl, thiazolyl, pyridonyl, 2-oxopiperidinyl, indolyl, quinolinyl, or isoquinolinyl, provided that if W is imidazolyl, the point of attachment of the imidazolyl moiety to $(CR_2^{1b})_p$ is selected from the group consisting of 4 or 5 position carbon of the imidazolyl moiety;

Y is selected from: —CH=CH—, —C≡C—, —C(O)—, —C($R^{10}$)$_2$—, —C(O$R^{10}$)$R^{10}$—, —CN($R^{10}$)$_2R^{10}$—, —OC($R^{10}$)$_2$—, N$R^{10}$C($R^{10}$)$_2$—, —C($R^{10}$)$_2$O—, —C($R^{10}$)$_2$N$R^{10}$—, —C(O)N$R^{10}$—, —N$R^{10}$C (O)—, O, —NC(O)$R^{10}$—, —NC(O)O$R^{10}$—, —S(O)$_2$N ($R^{10}$)—, —N($R^{10}$)S(O)$_2$—, or S(O)$_m$;

Z is $H_2$ or O;
m is 0, 1 or 2;
n is 0, 1, 2, 3 or 4;

p is 0, 1, 2, 3 or 4;

r is 0 to 5, provided that r is 0 when V is hydrogen; and u is 0 or 1;

or a pharmaceutically acceptable salt thereof.

3. A compound which inhibits Ras farnesyl-transferase having the Formula Ib:

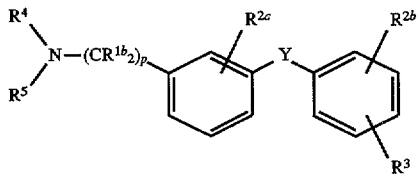

wherein:

$R^{1a}$ is independently selected from: hydrogen or $C_1$-$C_6$ alkyl;

$R^{1b}$ is independently selected from:
a) hydrogen,
b) unsubstituted or substituted aryl, unsubstituted or substituted heterocycle, unsubstituted or substituted $C_3$-$C_6$ cycloalkyl, $R^8O$—, —$N(R^8)_2$ or $C_2$-$C_6$ alkenyl,
c) $C_1$-$C_6$ alkyl unsubstituted or substituted with 1 or 2 substituents selected from: unsubstituted or substituted aryl, unsubstituted or substituted heterocycle, unsubstituted or substituted $C_3$-$C_6$ cycloalkyl, $C_2$-$C_6$ alkenyl, $R^8O$—, and —$N(R^8)_2$;

$R^{2a}$ and $R^{2b}$ are independently selected from:
a) hydrogen,
b) $C_1$-$C_6$ alkyl unsubstituted or substituted by a substituent selected from: $R^8O$—, —$N(R^8)_2$, and $R^9S(O)_m$—,
c) substituted or unsubstituted aryl, and
d) halogen selected from F, I, Cl and Br;

$R^3$ is selected from:
a) hydrogen,
b) $C_1$-$C_6$ alkyl unsubstituted or substituted by a substituent selected from: $R^8O$—, —$N(R^8)_2$ and $R^9S(O)_m$—,
c) substituted or unsubstituted aryl,
d) halogen selected from F, I, Cl and Br, and
e) —$CO_2R^8$;

$R^4$ and $R^5$ are independently selected from:
a) hydrogen, and b)
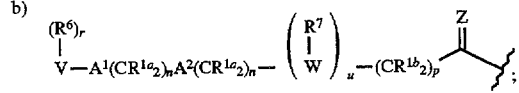

$R^6$ is selected from:
a) hydrogen,
b) substituted or unsubstituted aryl, $C_1$-$C_6$ alkyl, $C_2$-$C_6$ alkenyl, $C_2$-$C_6$ alkynyl, $C_1$-$C_6$ perfluoroalkyl, F, Cl, $R^8O$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and
c) $C_1$-$C_6$ alkyl substituted by $C_1$-$C_6$ perfluoroalkyl, $R^8O$—, $R^8C(O)NR^8$—, $(R^8)_2N$—$C(NR^8)$—, $R^8C(O)$—, $R^8OC(O)$—, —$N(R^8)_2$, or $R^9OC(O)NR^8$—;

$R^7$ is selected from:
a) hydrogen,
b) $C_2$-$C_6$ alkenyl, $C_2$-$C_6$ alkynyl, $C_1$-$C_6$ perfluoroalkyl, F, Cl, $R^8O$—, $R^9S(O)_m$—, $R^8C(O)$ $NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and
c) $C_1$-$C_6$ alkyl unsubstituted or substituted by $C_1$-$C_6$ perfluoroalkyl, F, Cl, $R^8O$—, $R^9S(O)_m$—, $R^8C(O)$ $NR^8$—, CN, $(R^8)_2N$—$C(NR^8)$—, $R^8C(O)$—, $R^8OC$ (O)—, —$N(R^8)_2$, or $R^9OC(O)NR^8$—;

$R^8$ is independently selected from hydrogen, $C_1$-$C_6$ alkyl, substituted or unsubstituted $C_1$-$C_6$ aralkyl and substituted or unsubstituted aryl;

$R^9$ is independently selected from $C_1$-$C_6$ alkyl and aryl;

$R^{10}$ is independently selected from hydrogen, $C_1$-$C_3$ alkyl and benzyl;

$A^1$ and $A^2$ are independently selected from: a bond, —CH=CH—, —C≡C—, —C(O)—, —C(O)$NR^8$—, O, —$N(R^8)$—, or $S(O)_m$;

V is selected from:
a) hydrogen,
b) heterocycle selected from pyrrolidinyl, imidazolyl, pyridinyl, thiazolyl, pyridonyl, 2-oxopiperidinyl, indolyl, quinolinyl, isoquinolinyl, and thienyl,
c) aryl,
d) $C_1$-$C_{20}$ alkyl wherein from 0 to 4 carbon atoms are replaced with a a heteroatom selected from O, S, and N, and
e) $C_2$-$C_{20}$ alkenyl, and
provided that V is not hydrogen if $A^1$ is $S(O)_m$ and V is not hydrogen if $A^1$ is a bond, n is 0 and $A^2$ is $S(O)_m$;

W is a heterocycle selected from pyrrolidinyl, imidazolyl, imidazolinyl, pyridinyl, thiazolyl, pyridonyl, 2-oxopiperidinyl, indolyl, quinolinyl, or isoquinolinyl, provided that if W is imidazolyl, the point of attachment of the imidazolyl moiety to $(CR_2^{1b})_p$ is selected from the group consisting of 4 or 5 position carbon of the imidazolyl moiety;

Y is selected from: —CH=CH—, —C≡C—, —C(O)—, —$C(R^{10})_2$—, —C(OR 10)$R^{10}$—, —$CN(R^{10})_2R^{10}$—, —$OC(R^{10})_2$—, —$NR^{10}C(R^{10})_2$—, —$C(R^{10})_2O$—, —$C(R^{10})_2NR^{10}$—, —$C(O)NR^{10}$—, —$NR^{10}C(O)$—, O, —$NC(O)R^{10}$—, —$NC(O)OR^{10}$—, —$S(O)_2N$ $(R^{10})$—, —$N(R^{10})S(O)_2$—, or $S(O)_m$;

Z is $H_2$ or O;

m is 0, 1 or 2;

n is 0, 1, 2, 3 or 4;

p is 0, 1, 2, 3 or 4;

r is 0 to 5, provided that r is 0 when V is hydrogen; and u is 0 or 1;

or a pharmaceutically acceptable salt thereof.

4. A compound which is:

N,N-bis(4-Imidazolemethyl)amino-3-[(3-carboxyphenyl)oxy]benzene

N,N-bis(4-Imidazolemethyl)amino-4-[(3-carboxyphenyl)oxy]benzene

N,N-bis(4-Imidazolemethyl)amino-3-[(3-carbomethoxyphenyl)oxy]benzene

N,N-bis(4-Imidazolemethyl)amino-4-[(3-carbomethoxyphenyl)oxy]benzene

N-(4-Imidazolemethyl)-N-(4-nitrobenzyl)aminomethyl-3-[(3-carboxyphenyl)oxy]benzene N-(4-Imidazolemethyl)-N-(4-nitrobenzyl)aminomethyl-3-[(3-carbomethoxyphenyl)oxy]benzene N-(4-Imidazolemethyl)-N-(4-nitrobenzyl)amino-3-(phenoxy)benzene N-(4-Imidazolemethyl)-N-(4-nitrobenzyl)amino-4-(phenoxy)benzene N-(4-Imidazolemethyl)-N-(4-nitrobenzyl)amino-4-(phenylthio)benzene N-Butyl-N-[1-(4-cyanobenzyl)-5-imidazolemethyl]amino-4-(phenoxy)benzene N-[1-(4-Cyanobenzyl)-5-imidazolemethyl]amino-4-(phenoxy)benzene N-(4-Imidazolemethyl)amino-3-[(3-carboxyphenyl)oxy]benzene 1-[N-(1-(4-cyanobenzyl)-5-imidazolylmethyl)-N-(4-cyanobenzyl)amino]-4-(phenoxy)benzene (±)-4-[(4-imidazolylmethyl)amino]pentyl- 1-(phenoxy)benzene 1-[(N-(1-(4-cyanobenzyl)-5-imidazolylmethyl)-N-(n-butyl)amino)methyl]-4-(phenoxy)benzene 4-[N-(1-(4-cyanobenzyl)-5-imidazolylmethyl)-N-(n-butyl)amino]-1-(phenylthio)benzene (±)-4-[N-(1-(4-cyanobenzyl)-4-imidazolylmethyl)-N-(n-butyl)amino]-1-(phenylsulfinyl)benzene 3-[N-(4-imidazolylmethyl)-N-(n-butyl)amino]-N-(phenyl)benzenesulfonamide or 1-[N-(1-(4-cyanobenzyl)-5-imidazolylmethyl)amino]-3-methoxy-4-phenylbenzene or a pharmaceutically acceptable salt or optical isomer thereof.

5. The compound according to claim 4 which is:

N-(4-Imidazolemethyl)-N-(4-nitrobenzyl)amino-3-(phenoxy)benzene

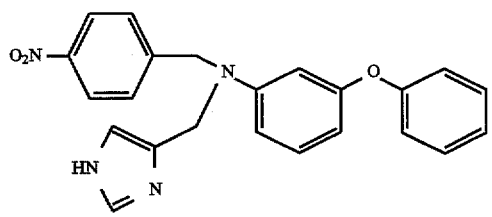

or a pharmaceutically acceptable salt thereof.

6. The compound according to claim 4 which is:

N-(4-Imidazolemethyl)-N-(4-nitrobenzyl)aminomethyl-3-[(3-carbomethoxyphenyl)oxy]benzene

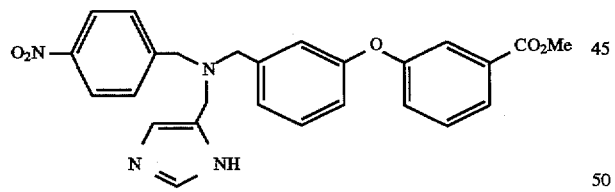

or a pharmaceutically acceptable salt thereof.

7. The compound according to claim 4 which is:

N-(4-Imidazolemethyl)amino-3-[(3-carboxyphenyl)oxy]benzene

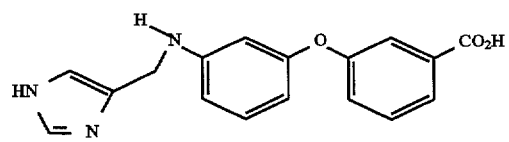

or a pharmaceutically acceptable salt thereof.

8. The compound according to claim 4 which is:

N,N-bis(4-Imidazolemethyl)amino-4-[(3-carbomethoxyphenyl)-oxy]benzene

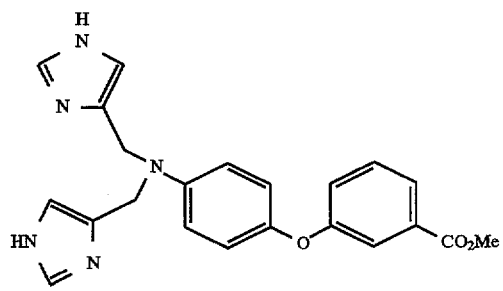

or a pharmaceutically acceptable salt thereof.

9. The compound according to claim 4 which is:

N-Butyl-N-[1-(4-cyanobenzyl)-5-imidazolemethyl]amino-4-(phenoxy)benzene

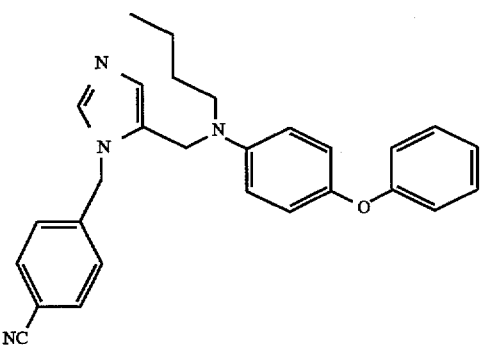

or a pharmaceutically acceptable salt thereof.

10. The compound according to claim 4 which is:

1-[N-(1-(4-cyanobenzyl)-5-imidazolylmethyl)-N-(4-cyanobenzyl)amino]-4-(phenoxy)benzene

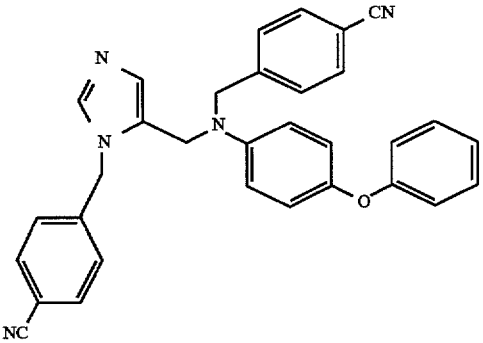

or a pharmaceutically acceptable salt thereof.

11. The compound according to claim 4 which is:

(±)-4-[N-(1-(4-cyanobenzyl)-4-imidazolylmethyl)-N-(n-butyl)amino]-1-(phenylsulfinyl)benzene

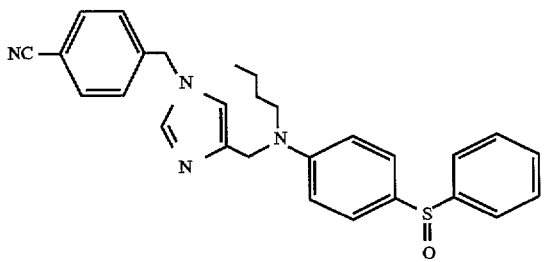

or a pharmaceutically acceptable salt thereof.

12. The compound according to claim 4 which is:
1-[N-(1-(4-cyanobenzyl)-5-imidazolylmethyl)amino]-3-methoxy-4-phenylbenzene

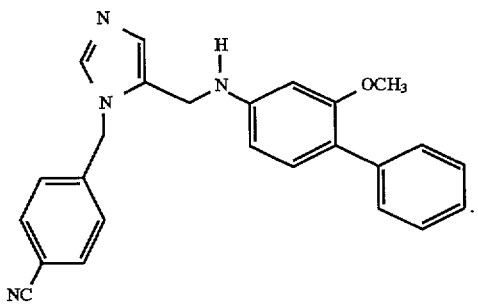

13. A pharmaceutical composition comprising a pharmaceutical carrier, and dispersed therein, a therapeutically effective amount of a compound of claim 1.

14. A pharmaceutical composition comprising a pharmaceutical carrier, and dispersed therein, a therapeutically effective amount of a compound of claim 2.

15. A pharmaceutical composition comprising a pharmaceutical carrier, and dispersed therein, a therapeutically effective amount of a compound of claim 3.

16. A pharmaceutical composition comprising a pharmaceutical carrier, and dispersed therein, a therapeutically effective amount of a compound of claim 4.

17. The compound according to claim 2 which inhibits Ras farnesyl-transferase having the Formula Ia:

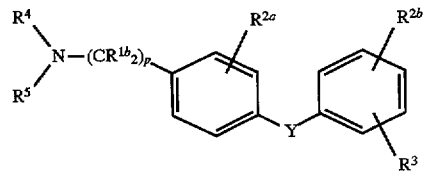

wherein:
$R^{1a}$ is independently selected from: hydrogen or $C_1$-$C_6$ alkyl;
$R^{1b}$ is independently selected from:
  a) hydrogen,
  b) unsubstituted or substituted aryl, unsubstituted or substituted heterocycle, unsubstituted or substituted $C_3$-$C_6$ cycloalkyl, $R^8O$—, —$N(R^8)_2$ or $C_2$-$C_6$ alkenyl,
  c) $C_1$-$C_6$ alkyl unsubstituted or substituted with 1 or 2 substituents selected from: unsubstituted or substituted aryl, unsubstituted or substituted heterocycle, unsubstituted or substituted $C_3$-$C_6$ cycloalkyl, $C_2$-$C_6$ alkenyl, $R^8O$—, and —$N(R^8)_2$;
$R^{2a}$ and $R^{2b}$ are independently selected from:
  a) hydrogen,
  b) $C_1$-$C_6$ alkyl unsubstituted or substituted by a substituent selected from: $R^8O$—, —$N(R^8)_2$, and $R^9S(O)_m$—,
  c) substituted or unsubstituted aryl, and
  d) halogen selected from F, I, Cl and Br;
$R^3$ is selected from:
  a) hydrogen,
  b) $C_1$-$C_6$ alkyl unsubstituted or substituted by a substituent selected from: $R^8O$—, —$N(R^8)_2$ and $R^9S(O)_m$—,
  c) substituted or unsubstituted aryl,
  d) halogen selected from F, I, Cl and Br, and
  e) —$CO_2R^8$;
$R^4$ is

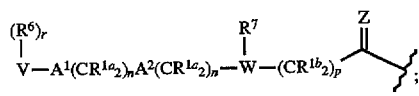

wherein
W is selected from imidazolyl and pyridinyl, provided that if W is imidazolyl, the point of attachment of the imidazolyl moiety to $(CR_2^{1b})_p$ is selected from the group consisting of 4 or 5 position carbon of the imidazolyl moiety;
$R^5$ is selected from:
  a) hydrogen, and b) 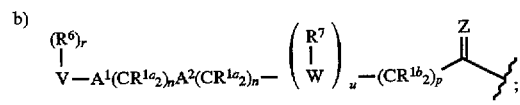

wherein
W is a heterocycle selected from pyrrolidinyl, imidazolyl, imidazolinyl, pyridinyl, thiazolyl, pyridonyl, 2-oxopiperidinyl, indolyl, quinolinyl, or isoquinolinyl, provided that if W is imidazolyl, the point of attachment of the imidazolyl moiety to $(CR_2^{1b})_p$ is selected from the group consisting of 4 or 5 position carbon of the imidazolyl moiety;
$R^6$ is selected from:
  a) hydrogen,
  b) substituted or unsubstituted aryl, $C_1$-$C_6$ alkyl, $C_2$-$C_6$ alkenyl, $C_2$-$C_6$ alkynyl, $C_1$-$C_6$ perfluoroalkyl, F, Cl, $R^8O$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and
  c) $C_1$-$C_6$ alkyl substituted by $C_1$-$C_6$ perfluoroalkyl, $R^8O$—, $R^8C(O)NR^8$—, $(R^8)_2N$—$C(NR^8)$—, $R^8C(O)$—, $R^8OC(O)$—, —$N(R^8)_2$, or $R^9OC(O)NR^8$—;
$R^7$ is selected from:
  a) hydrogen,
  b) $C_2$-$C_6$ alkenyl, $C_2$-$C_6$ alkynyl, $C_1$-$C_6$ perfluoroalkyl, F, Cl, $R^8O$—, $R^9S(O)_m$—, $R^8C(O)NR^8$—, CN, $NO_2$, $(R^8)_2N$—$C(NR^8)$—, $R^8C(O)$—, $R^8OC(O)$—, —$N(R^8)_2$, or $R^9OC(O)NR^8$—, and
  c) $C_1$-$C_6$ alkyl unsubstituted or substituted by $C_1$-$C_6$ perfluoroalkyl, F, Cl, $R^8O$—, $R^9S(O)_m$—, $R^8C(O)NR^8$—, CN, $(R^8)_2N$—$C(NR^8)$—, $R^8C(O)$—, $R^8OC(O)$—, —$N(R^8)_2$, or $R^9OC(O)NR^8$—;
$R^8$ is independently selected from hydrogen, $C_1$-$C_6$ alkyl, substituted or unsubstituted $C_1$-$C_6$ aralkyl and substituted or unsubstituted aryl;

$R^9$ is independently selected from $C_1-C_6$ alkyl and aryl;

$R^{10}$ is independently selected from hydrogen, $C_1-C_3$ alkyl and benzyl;

$A^1$ and $A^2$ are independently selected from: a bond, —CH=CH—, —C≡C—, —C(O)—, —C(O)NR$^8$—, O, —N(R$^8$)—, or S(O)$_m$;

V is selected from:
 a) hydrogen,
 b) heterocycle selected from pyrrolidinyl, imidazolyl, pyridinyl, thiazolyl, pyridonyl, 2-oxopiperidinyl, indolyl, quinolinyl, isoquinolinyl, and thienyl,
 c) aryl,
 d) $C_1-C_{20}$ alkyl wherein from 0 to 4 carbon atoms are replaced with a a heteroatom selected from O, S, and N, and
 e) $C_2-C_{20}$ alkenyl, and provided that V is not hydrogen if $A^1$ is S(O)$_m$ and V is not hydrogen if $A^1$ is a bond, n is 0 and $A^2$ is S(O)$_m$;

Y is selected from: —CH=CH—, —C≡C—, —C(O)—, —C(R$^{10}$)$_2$—, —C(OR$^{10}$)R$^{10}$—, —CN(R$^{10}$)$_2$R$^{10}$—, —OC(R$^{10}$)$_2$—, —NR$^{10}$C(R$^{10}$)$_2$—, —NC(O)R$^{10}$—, —NC(O)OR$^{10}$—, —S(O)$_2$N(R$^{10}$)—, —N(R$^{10}$)S(O)$_2$—, or S(O)$_m$;

Z is $H_2$ or O;

m is 0, 1 or 2;

n is 0, 1, 2, 3 or 4;

p is 0, 1, 2, 3 or 4;

r is 0 to 5, provided that r is 0 when V is hydrogen; and u is 0 or 1;

or a pharmaceutically acceptable salt thereof.

18. A method for inhibiting farnesyl-protein transferase which comprises administering to a mammal in need thereof a therapeutically effective amount of the composition of claim 14.

19. A method for inhibiting farnesyl-protein transferase which comprises administering to a mammal in need thereof a therapeutically effective amount of the composition of claim 15.

20. A method for inhibiting farnesyl-protein transferase which comprises administering to a mammal in need thereof a therapeutically effective amount of the composition of claim 16.

21. The compound according to claim 3 of the formula Ib:

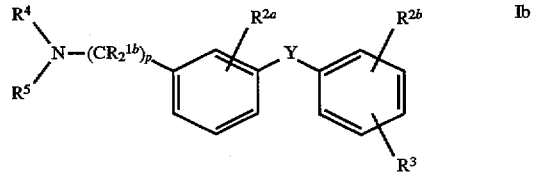

wherein:

$R^{1a}$ is independently selected from: hydrogen or $C_1-C_6$ alkyl;

$R^{1b}$ is independently selected from:
 a) hydrogen,
 b) unsubstituted or substituted aryl, unsubstituted or substituted heterocycle, unsubstituted or substituted $C_3-C_6$ cycloalkyl, $R^8$O—, —N(R$^8$)$_2$ or $C_2-C_6$ alkenyl,
 c) $C_1-C_6$ alkyl unsubstituted or substituted with 1 or 2 substituents selected from: unsubstituted or substituted aryl, unsubstituted or substituted heterocycle, unsubstituted or substituted $C_3-C_6$ cycloalkyl, $C_2-C_6$ alkenyl, $R^8$O—, and —N(R$^8$)$_2$;

$R^{2a}$ and $R^{2b}$ are independently selected from:
 a) hydrogen,
 b) $C_1-C_6$ alkyl unsubstituted or substituted by a substituent selected from: R$^8$O—, —N(R$^8$)$_2$, and R$^9$S(O)$_m$—,
 c) substituted or unsubstituted aryl, and
 d) halogen selected from F, I, Cl and Br;

$R^3$ is selected from:
 a) hydrogen,
 b) $C_1-C_6$ alkyl unsubstituted or substituted by a substituent selected from: R$^8$O—, —N(R$^8$)$_2$ and R$^9$S(O)$_m$—,
 c) substituted or unsubstituted aryl,
 d) halogen selected from F, I, Cl and Br, and
 e) —CO$_2$R$^8$;

$R^4$ is

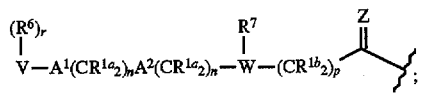

wherein

W is selected from imidazolyl and pyridinyl, provided that if W is imidazolyl, the point of attachment of the imidazolyl moiety to (CR$_2^{1b}$)$_p$ is selected from the group consisting of 4 or 5 position carbon of the imidazolyl moiety;

$R^5$ is selected from:
 a) hydrogen, and
 b)

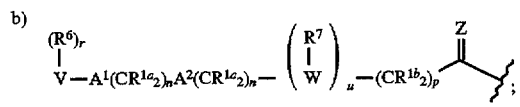

wherein

W is a heterocycle selected from pyrrolidinyl, imidazolyl, imidazolinyl, pyridinyl, thiazolyl, pyridonyl, 2-oxopiperidinyl, indolyl, quinolinyl, or isoquinolinyl, provided that if W is imidazolyl, the point of attachment of the imidazolyl moiety to (CR$_2^{1b}$)$_p$ is selected from the group consisting of 4 or 5 position carbon of the imidazolyl moiety;

$R^6$ is selected from:
 a) hydrogen,
 b) substituted or unsubstituted aryl, $C_1-C_6$ alkyl, $C_2-C_6$ alkenyl, $C_2-C_6$ alkynyl, $C_1-C_6$ perfluoroalkyl, F, Cl, R$^8$O—, R$^8$C(O)NR$^8$—, CN, NO$_2$, (R$^8$)$_2$N—C(NR$^8$)—, R$^8$C(O)—, R$^8$OC(O)—, —N(R$^8$)$_2$, or R$^9$OC(O)NR$^8$—, and
 c) $C_1-C_6$ alkyl substituted by $C_1-C_6$ perfluoroalkyl, R$^8$O—, R$^8$C(O)NR$^8$—, (R$^8$)$_2$N—C(NR$^8$)—, R$^8$C(O)—, R$^8$OC(O)—, —N(R$^8$)$_2$, or R$^9$OC(O)NR$^8$—;

$R^7$ is selected from:
 a) hydrogen,
 b) $C_2-C_6$ alkenyl, $C_2-C_6$ alkynyl, $C_1-C_6$ perfluoroalkyl, F, Cl, R$^8$O—, R$^9$S(O)$_m$—, R$^8$C(O)NR$^8$—, CN, NO$_2$, (R$^8$)$_2$N—C(NR$^8$)—, R$^8$C(O)—, R$^8$OC(O)—, —N(R$^8$)$_2$, or R$^9$OC(O)NR$^8$—, and
 c) $C_1-C_6$ alkyl unsubstituted or substituted by $C_1-C_6$ perfluoroalkyl, F, Cl, R$^8$O—, R$^9$S(O)$_m$—, R$^8$C(O)NR$^8$—, CN, (R$^8$)$_2$N—C(NR$^8$)—, R$^8$C(O)—, R$^8$OC(O)—, —N(R$^8$)$_2$, or R$^9$OC(O)NR$^8$—;

$R^8$ is independently selected from hydrogen, $C_1-C_6$ alkyl, substituted or unsubstituted $C_1-C_6$ aralkyl and substituted or unsubstituted aryl;

$R^9$ is independently selected from $C_1$–$C_6$ alkyl and aryl;

$R^{10}$ is independently selected from hydrogen, $C_1$–$C_3$ alkyl and benzyl;

$A^1$ and $A^2$ are independently selected from: a bond, —CH=CH—, —C≡C—, —C(O)—, —C(O)NR$^8$—, O, —N(R$^8$)—, or S(O)$_m$;

V is selected from:
  a) hydrogen,
  b) heterocycle selected from pyrrolidinyl, imidazolyl, pyridinyl, thiazolyl, pyridonyl, 2-oxopiperidinyl, indolyl, quinolinyl, isoquinolinyl, and thienyl,
  c) aryl,
  d) $C_1$–$C_{20}$ alkyl wherein from 0 to 4 carbon atoms are replaced with a a heteroatom selected from O, S, and N, and
  e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

W is a heterocycle selected from pyrrolidinyl, imidazolyl, imidazolinyl, pyridinyl, thiazolyl, pyridonyl, 2-oxopiperidinyl, indolyl, quinolinyl, or isoquinolinyl, provided that if W is imidazolyl, the point of attachment of the imidazolyl moiety to $(CR_2^{1b})_p$ is selected from the group consisting of 4 or 5 position carbon of Y is selected from: —CH=CH—, —C≡C—, —C(O)—, —C(R$^{10}$)$_2$—, —C(OR$^{10}$)R$^{10}$—, —CN(R$^{10}$)$_2$R$^{10}$—, —OC(R$^{10}$)$_2$—, —NR$^{10}$C(R$^{10}$)$_2$—, —C(R$^{10}$)$_2$O—, —C(R$^{10}$)$_2$NR$^{10}$—, —C(O)NR$^{10}$—, —NR$^{10}$C(O)—, O, —NC(O)R$^{10}$—, —NC(O)OR$^{10}$—, —S(O)$_2$N(R$^{10}$)—, —N(R$^{10}$)S(O)$_2$—, or S(O)$_m$;

Z is $H_2$ or O;

m is 0, 1 or 2;

n is 0, 1, 2, 3 or 4;

p is 0, 1, 2, 3 or 4;

r is 0 to 5, provided that r is 0 when V is hydrogen; and u is 0 or 1;

or a pharmaceutically acceptable salt thereof.

22. A method for treating cancer which comprises administering to a mammal in need thereof a therapeutically effective amount of a composition of claim 14.

23. A method for treating cancer which comprises administering to a mammal in need thereof a therapeutically effective amount of a composition of claim 15.

24. A method for treating cancer which comprises administering to a mammal in need thereof a therapeutically effective amount of a composition of claim 16.

25. A method for inhibiting farnesyl-protein transferase which comprises administering to a mammal in need thereof a therapeutically effective amount of the composition which comprises a therapeutically effective amount of a compound of the Formula I:

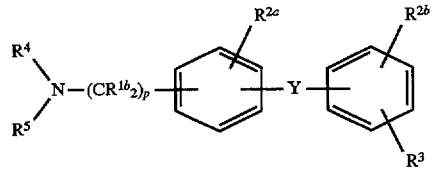

wherein:

$R^{1a}$ and $R^{1b}$ are independently selected from:
  a) hydrogen,
  b) unsubstituted or substituted aryl, unsubstituted or substituted heterocycle, unsubstituted or substituted $C_3$–$C_6$ cycloalkyl, $C_2$–$C_6$ alkenyl, $C_2$–$C_6$ alkynyl, R$^8$O—, R$^9$S(O)$_m$—, R$^8$C(O)NR$^8$—, CN, NO$_2$, (R$^8$)$_2$N—C(NR$^8$)—, R$^8$C(O)—, R$^8$OC(O)—, N$_3$, —N(R$^8$)$_2$, or R$^9$OC(O)NR$^8$—,
  c) $C_1$–$C_6$ alkyl unsubstituted or substituted by unsubstituted or substituted aryl, unsubstituted or substituted heterocyclic, unsubstituted or substituted $C_3$–$C_6$ cycloalkyl, $C_2$–$C_6$ alkenyl, $C_2$–$C_6$ alkynyl, R$^8$O—, R$^9$S(O)$_m$—, R$^8$C(O)NR$^8$—, CN, (R$^8$)$_2$N—C(NR$^8$)—, R$^8$C(O)—, R$^8$OC(O)—, N$_3$, —N(R$^8$)$_2$, or R$^9$OC(O)—NR$^8$—;

$R^{2a}$, $R^{2b}$ and $R^3$ are independently selected from:
  a) hydrogen,
  b) $C_1$–$C_6$ alkyl unsubstituted or substituted by $C_2$–$C_6$ alkenyl, R$^8$O—, R$^9$S(O)$_m$—, R$^8$C(O)NR$^8$—, CN, N$_3$, (R$^8$)$_2$N—C(NR$^8$)—, R$^8$C(O)—, R$^8$OC(O)—, —N(R$^8$)$_2$, or R$^9$OC(O)NR$^8$—,
  c) unsubstituted or substituted aryl, unsubstituted or substituted heterocycle, unsubstituted or substituted cycloalkyl, alkenyl, R$^8$O—, R$^9$S(O)$_m$—, R$^8$C(O)NR$^8$—, CN, NO$_2$, (R$^8$)$_2$N—C(NR$^8$)—, R$^8$C(O)—, R$^8$OC(O)—, N$_3$, —N(R$^8$)$_2$, halogen or R$^9$OC(O)NR$^8$—, and
  d) $C_1$–$C_6$ alkyl substituted with an unsubstituted or substituted group selected from aryl, heterocyclic and $C_3$–$C_{10}$ cycloalkyl;

$R^4$ and $R^5$ are independently selected from:
  a) hydrogen, and b)
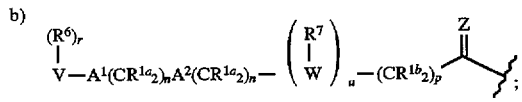

$R^6$ is independently selected from:
  a) hydrogen,
  b) unsubstituted or substituted aryl, unsubstituted or substituted heterocycle, unsubstituted or substituted $C_3$–$C_6$ cycloalkyl, $C_2$–$C_6$ alkenyl, $C_2$–$C_6$ alkynyl, $C_1$–$C_6$ perfluoroalkyl, F, Cl, Br, R$^8$O—, R$^9$S(O)$_m$—, R$^8$C(O)NR$^8$—, CN, NO$_2$, R$^8_2$N—C(NR$^8$)—, R$^8$C(O)—, R$^8$OC(O)—, N$_3$, —N(R$^8$)$_2$, or R$^9$OC(O)NR$^8$—, and
  c) $C_1$–$C_6$ alkyl unsubstituted or substituted by unsubstituted or substituted aryl, unsubstituted or substituted heterocycle, unsubstituted or substituted $C_3$–$C_6$ cycloalkyl, $C_2$–$C_6$ alkenyl, $C_2$–$C_6$ alkynyl, $C_1$–$C_6$ perfluoroalkyl, F, Cl, Br, R$^8$O—, R$^9$S(O)$_m$—, R$^8$C(O)NH—, CN, H$_2$N—C(NH)—, R$^8$C(O)—, R$^8$OC(O)—, N$_3$, —N(R$^8$)$_2$, or R$^8$OC(O)NH—;

$R^7$ is selected from:
  a) hydrogen,
  b) $C_2$–$C_6$ alkenyl, $C_2$–$C_6$ alkynyl, $C_1$–$C_6$ perfluoroalkyl, F, Cl, Br, R$^8$O—, R$^9$S(O)$_m$—, R$^8$C(O)NR$^8$—, CN, NO$_2$, (R$^8$)$_2$N—C—(NR$^8$)—, R$^8$C(O)—, R$^8$OC(O)—, N$_3$, —N(R$^8$)$_2$, or R$^9$OC(O)NR$^8$—, and
  c) $C_1$–$C_6$ alkyl unsubstituted or substituted by $C_1$–$C_6$ perfluoroalkyl, F, Cl, Br, R$^8$O—, R$^9$S(O)$_m$—, R$^8$C(O)NR$^8$—, CN, (R$^8$)$_2$N—C(NR$^8$)—, R$^8$C(O)—, R$^8$OC(O)—, N$_3$, —N(R$^8$)$_2$, or R$^9$OC(O)NR$^8$—;

$R^8$ is independently selected from hydrogen, $C_1$–$C_6$ alkyl, substituted or unsubstituted $C_1$–$C_6$ aralkyl and substituted or unsubstituted aryl;

$R^9$ is independently selected from $C_1$–$C_6$ alkyl and aryl;

$R^{10}$ is independently selected from hydrogen, $C_1$–$C_6$ alkyl, substituted or unsubstituted $C_1$–$C_6$ aralkyl and substituted or unsubstituted aryl;

$A^1$ and $A^2$ are independently selected from: a bond, —CH=CH—, —C≡C—, —C(O)—, —C(O)NR$^8$—, —NR$^8$C(O)—, O, —N(R$^8$)—, —S(O)$_2$N(R$^8$)—, —N(R$^8$)S(O)$_2$—, or S(O)$_m$;

V is selected from:
a) hydrogen,
b) heterocycle,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, provided that V is not hydrogen if $A^1$ is S(O)$_m$ and V is not hydrogen if $A^1$ is a bond, n is 0 and $A^2$ is S(O)$_m$;

W is a heterocycle;

Y is selected from: a bond, —C(R$^{10}$)=C(R$^{10}$)—, —C≡C—, —C(O)—, —C(R$^{10}$)$_2$—, —C(OR$^{10}$)R$^{10}$—, —CN(R$^{10}$)$_2$R$^{10}$—, —OC(R$^{10}$)$_2$—, —NR$^{10}$C(R$^{10}$)$_2$—, —C(R$^{10}$)$_2$O—, —C(R$^{10}$)$_2$NR$^{10}$—, —C(O)NR$^{10}$—, —NR$^{10}$C(O), O, —NC(O)R$^{10}$—, —NC(O)OR$^{10}$—, —S(O)$_2$N(R$^{10}$)—, —N(R$^{10}$)S(O)$_2$—, or S(O)$_m$;

Z is H$_2$ or O;

m is 0, 1 or 2;

n is 0, 1, 2, 3 or 4;

p is 0, 1, 2, 3 or 4;

r is 0 to 5, provided that r is 0 when V is hydrogen; and u is 0 or 1;

or a pharmaceutically acceptable salt thereof.

26. A method for treating cancer which comprises administering to a mammal in need thereof a therapeutically effective amount of the composition which comprises a therapeutically effective amount of a compound of the Formula I:

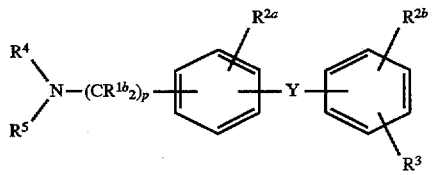

wherein:

$R^{1a}$ and $R^{1b}$ are independently selected from:
a) hydrogen,
b) unsubstituted or substituted aryl, unsubstituted or substituted heterocycle, unsubstituted or substituted $C_3$–$C_6$ cycloalkyl, $C_2$–$C_6$ alkenyl, $C_2$–$C_6$ alkynyl, R$^8$O—, R$^9$S(O)$_m$—, R$^8$C(O)NR$^8$—, CN, NO$_2$, (R$^8$)$_2$N—C(NR$^8$)—, R$^8$C(O)—, R$^8$OC(O)—, N$_3$, —N(R$^8$)$_2$, or R$^9$OC(O)NR$^8$—,
c) $C_1$–$C_6$ alkyl unsubstituted or substituted by unsubstituted or substituted aryl, unsubstituted or substituted heterocyclic, unsubstituted or substituted $C_3$–$C_6$ cycloalkyl, $C_2$–$C_6$ alkenyl, $C_2$–$C_6$ alkynyl, R$^8$O—, R$^9$S(O)$_m$—, R$^8$C(O)NR$^8$—, CN, (R$^8$)$_2$N—C(NR$^8$)—, R$^8$C(O)—, R$^8$OC(O)—, N$_3$, —N(R$^8$)$_2$, or R$^9$OC(O)—NR$^8$—;

$R^{2a}$, $R^{2b}$ and $R^3$ are independently selected from:
a) hydrogen,
b) $C_1$–$C_6$ alkyl unsubstituted or substituted by $C_2$–$C_6$ alkenyl, R$^8$O—, R$^9$S(O)$_m$—, R$^8$C(O)NR$^8$—, CN, N$_3$, (R$^8$)$_2$N—C(NR$^8$)—, R$^8$C(O)—, R$^8$OC(O)—, —N(R$^8$)$_2$, or R$^9$OC(O)NR$^8$—,
c) unsubstituted or substituted aryl, unsubstituted or substituted heterocycle, unsubstituted or substituted cycloalkyl, alkenyl, R$^8$O—, R$^9$S(O)$_m$—, R$^8$C(O)NR$^8$—, CN, NO$_2$, (R$^8$)$_2$N—C(NR$^8$)—, R$^8$C(O)—, R$^8$OC(O)—, N$_3$, —N(R$^8$)$_2$, halogen or R$^9$OC(O)NR$^8$—, and
d) $C_1$–$C_6$ alkyl substituted with an unsubstituted or substituted group selected from aryl, heterocyclic and $C_3$–$C_{10}$ cycloalkyl;

$R^4$ and $R^5$ are independently selected from:
a) hydrogen, and b)
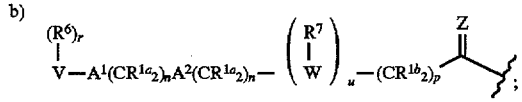

$R^6$ is independently selected from:
a) hydrogen,
b) unsubstituted or substituted aryl, unsubstituted or substituted heterocycle, unsubstituted or substituted $C_3$–$C_6$ cycloalkyl, $C_2$–$C_6$ alkenyl, $C_2$–$C_6$ alkynyl, $C_1$–$C_6$ perfluoroalkyl, F, Cl, Br, R$^8$O—, R$^9$S(O)$_m$—, R$^8$C(O)NR$^8$—, CN, NO$_2$, R$^8$$_2$N—C(NR$^8$)—, R$^8$C(O)—, R$^8$OC(O)—, N$_3$, —N(R$^8$)$_2$, or R$^9$OC(O)NR$^8$—, and
c) $C_1$–$C_6$ alkyl unsubstituted or substituted by unsubstituted or substituted aryl, unsubstituted or substituted heterocycle, unsubstituted or substituted $C_3$–$C_6$ cycloalkyl, $C_2$–$C_6$ alkenyl, $C_2$–$C_6$ alkynyl, $C_1$–$C_6$ perfluoroalkyl, F, Cl, Br, R$^8$O—, R$^9$S(O)$_m$—, R$^8$C(O)NH—, CN, H$_2$N—C(NH)—, R$^8$C(O)—, R$^8$OC(O)—, N$_3$, —N(R$^8$)$_2$, or R$^8$OC(O)NH—;

$R^7$ is selected from:
a) hydrogen,
b) $C_2$–$C_6$ alkenyl, $C_2$–$C_6$ alkynyl, $C_1$–$C_6$ perfluoroalkyl, F, Cl, Br, R$^8$O—, R$^9$S(O)$_m$—, R$^8$C(O)NR$^8$—, CN, NO$_2$, (R$^8$$_2$N—C—(NR$^8$)—, R$^8$C(O)—, R$^8$OC(O)—, N$_3$, —N(R$^8$)$_2$, or R$^9$OC(O)NR$^8$—, and
c) $C_1$–$C_6$ alkyl unsubstituted or substituted by $C_1$–$C_6$ perfluoroalkyl, F, Cl, Br, R$^8$O—, R$^9$S(O)$_m$—, R$^8$C(O)NR$^8$—, CN, (R$^8$)$_2$N—C(NR$^8$)—, R$^8$C(O)—, R$^8$OC(O)—, N$_3$, —N(R$^8$)$_2$, or R$^9$OC(O)NR$^8$—;

$R^8$ is independently selected from hydrogen, $C_1$–$C_6$ alkyl, substituted or unsubstituted $C_1$–$C_6$ aralkyl and substituted or unsubstituted aryl;

$R^9$ is independently selected from $C_1$–$C_6$ alkyl and aryl;

$R^{10}$ is independently selected from hydrogen, $C_1$–$C_6$ alkyl, substituted or unsubstituted $C_1$–$C_6$ aralkyl and substituted or unsubstituted aryl;

$A^1$ and $A^2$ are independently selected from: a bond, —CH=CH—, —C≡C—, —C(O)—, —C(O)NR$^8$—, —NR$^8$C(O)—, O, —N(R$^8$)—, —S(O)$_2$N(R$^8$)—, —N(R$^8$)S(O)$_2$—, or S(O)$_m$;

V is selected from:
a) hydrogen,
b) heterocycle,
c) aryl,
d) $C_1$–$C_{20}$ alkyl wherein from 0 to 4 carbon atoms are replaced with a a heteroatom selected from O, S, and N, and
e) $C_2$–$C_{20}$ alkenyl, provided that V is not hydrogen if $A^1$ is S(O)$_m$ and V is not hydrogen if $A^1$ is a bond, n is 0 and $A^2$ is S(O)$_m$;

W is a heterocycle;

Y is selected from: a bond, —C(R$^{10}$)=C(R$^{10}$)—, —C≡C—, —C(O)—, —C(R$^{10}$)$_2$—, —C(OR$^{10}$)R$^{10}$—, —CN(R$^{10}$)$_2$R$^{10}$—, —OC(R$^{10}$)$_2$—, —NR$^{10}$C(R$^{10}$)$_2$—,
—C(R$^{10}$)$_2$O—, —C(R$^{10}$)$_2$NR$^{10}$—, —C(O)NR$^{10}$—,
—NR$^{10}$C(O)—, O, —NC(O)R$^{10}$—, —NC(O)OR$^{10}$—,
—S(O$_2$)N(R$^{10}$)—, —N(R$^{10}$)S(O$_2$)—, or S(O)$_m$;

Z is H$_2$ or O;

m is 0, 1 or 2;

n is 0, 1, 2, 3 or 4;

p is 0, 1, 2, 3 or 4;

r is 0 to 5, provided that r is 0 when V is hydrogen; and u is 0 or 1;

or a pharmaceutically acceptable salt thereof.

* * * * *